United States Patent
Rea et al.

(10) Patent No.: US 7,522,762 B2
(45) Date of Patent: Apr. 21, 2009

(54) DETECTION, RESOLUTION, AND IDENTIFICATION OF ARRAYED ELEMENTS

(75) Inventors: Larry Rea, Lafayette, CO (US); David D. Clark, Longmont, CO (US); Rob Jenison, Boulder, CO (US); Diana Maul, Thornton, CO (US)

(73) Assignee: Inverness Medical-Biostar, Inc., Waltham, MA (US)

( * ) Notice: Subject to any disclaimer, the term of this patent is extended or adjusted under 35 U.S.C. 154(b) by 487 days.

(21) Appl. No.: 10/417,883

(22) Filed: Apr. 16, 2003

(65) Prior Publication Data

US 2004/0208350 A1 Oct. 21, 2004

(51) Int. Cl.
*G06K 9/00* (2006.01)
*G01R 31/26* (2006.01)
(52) U.S. Cl. .......................................... 382/141; 438/16
(58) Field of Classification Search ........................ None
See application file for complete search history.

(56) References Cited

U.S. PATENT DOCUMENTS

| | | | |
|---|---|---|---|
| 3,748,042 | A | 7/1973 | Diamantides |
| 5,319,436 | A | 6/1994 | Manns et al. |
| 5,494,829 | A | 2/1996 | Sandstrom et al. |
| 5,550,063 | A | 8/1996 | Bogart |
| 5,552,272 | A | 9/1996 | Bogart |
| 5,629,214 | A | 5/1997 | Crosby |
| 5,631,171 | A | 5/1997 | Sandstrom et al. |
| 5,639,671 | A | 6/1997 | Bogart et al. |
| 5,782,361 | A | 7/1998 | Kakizaki et al. |
| 5,955,377 | A | 9/1999 | Maul et al. |
| 5,986,279 | A | 11/1999 | Dewaele |
| 6,060,237 | A | 5/2000 | Nygren et al. |
| 6,287,783 | B1 | 9/2001 | Maynard et al. |
| 6,292,586 | B1 | 9/2001 | Kawakami et al. |
| 6,355,429 | B1 | 3/2002 | Nygren et al. |

(Continued)

FOREIGN PATENT DOCUMENTS

WO      WO 01/92870      12/2001

OTHER PUBLICATIONS

Notification Of Transmittal of International Search Report and International Preliminary Examination Report dated May 1, 2006 (9 pages).

(Continued)

*Primary Examiner*—Charles Kim
(74) *Attorney, Agent, or Firm*—Swanson & Bratschun L.L.C.

(57) ABSTRACT

An image analysis workstation for analyzing optical thin film arrays is disclosed. One disclosed embodiment relates to individual arrays that comprise a single optical thin film test surface that provides a plurality of discretely addressable locations, each comprising an immobilized capture reagent for an analyte of interest. These are referred to herein as "arrayed optical thin film test surfaces." Preferably, an individual arrayed optical thin film test surface comprises at least 4, more preferably at least 16, even more preferably at least 32, still more preferably at least 64, and most preferably 128 or more discretely addressable locations. One or more of the discretely addressable locations may provide control signals (e.g., for normalizing signals and/or that act as positive and/or negative controls) or fiducial signals (i.e., information that is used to determine the relative alignment of the arrayed optical thin film test surface within the device.

9 Claims, 19 Drawing Sheets

U.S. PATENT DOCUMENTS

| | | |
|---|---|---|
| 6,396,942 B1 | 5/2002 | Chang et al. |
| 6,410,252 B1 | 6/2002 | Lehmann et al. |
| 6,441,894 B1 | 8/2002 | Manian et al. |
| 6,483,585 B1 | 11/2002 | Yang |
| 2003/0016883 A1 | 1/2003 | Baron |
| 2003/0038957 A1 | 2/2003 | Sharman |
| 2003/0096302 A1* | 5/2003 | Yguerabide et al. .......... 435/7.1 |
| 2003/0148542 A1* | 8/2003 | Pawlak et al. ............... 436/518 |
| 2005/0040907 A1* | 2/2005 | Nebrigic .................... 332/118 |

OTHER PUBLICATIONS

Ando, "Consistent Gradient Operators." *IEEE Transactions on Pattern Analysis and Machine Intelligence*, 22(3): 252-265, 2000.

* cited by examiner

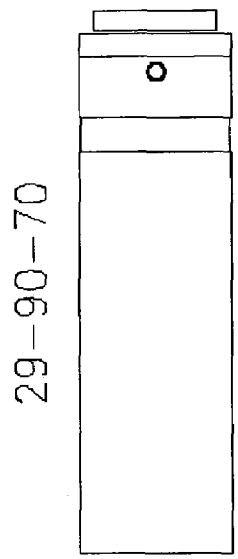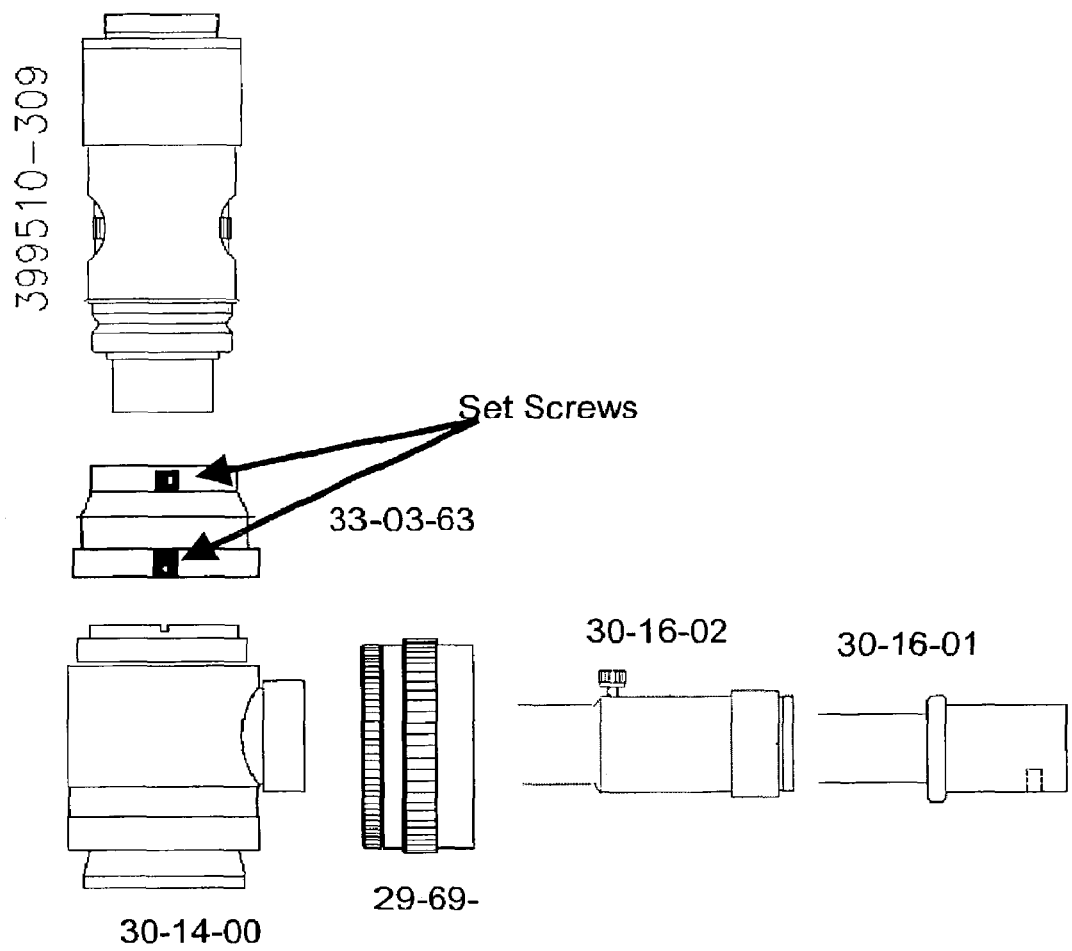
FIG. 3

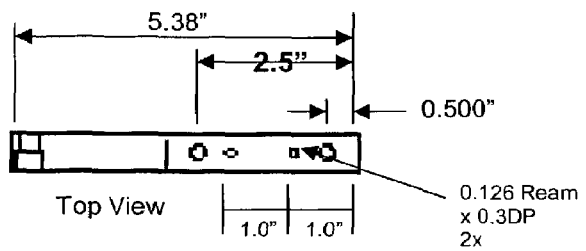
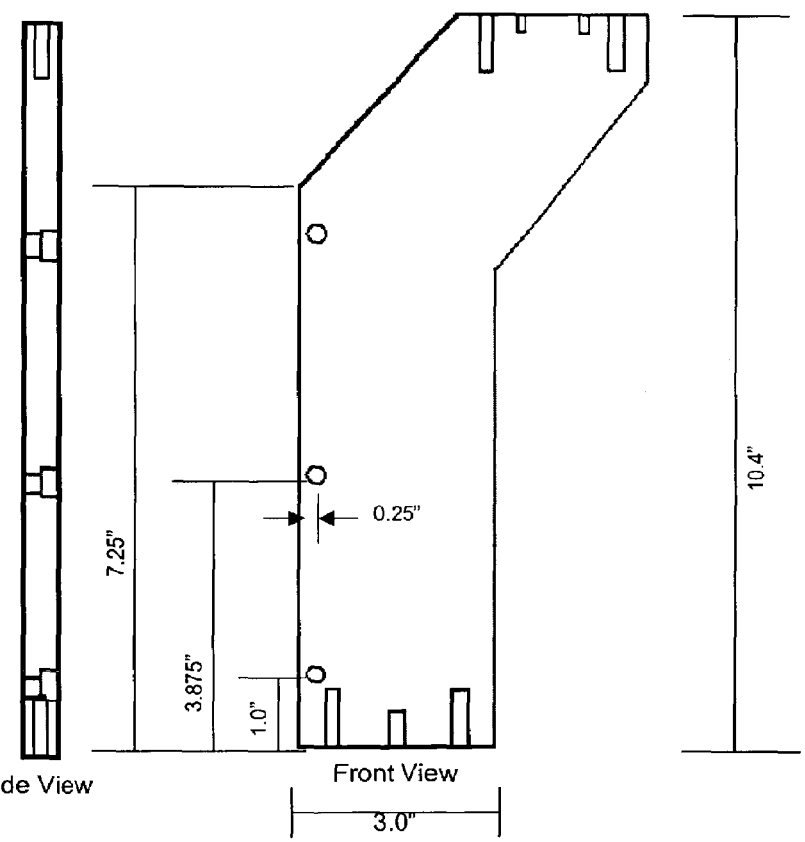
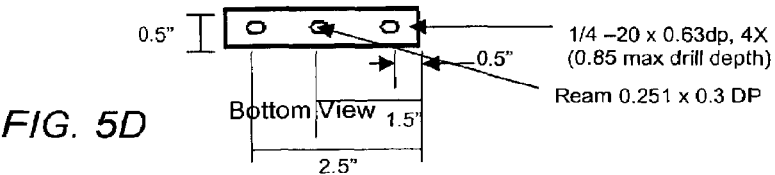
FIG. 5B
FIG. 5A
FIG. 5C
FIG. 5D

FIG. 6B
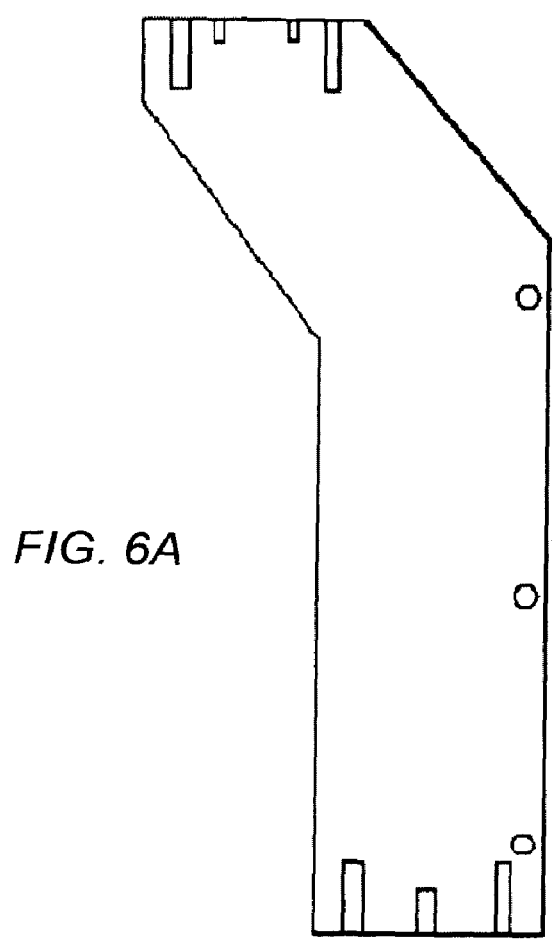
FIG. 6C
FIG. 6A
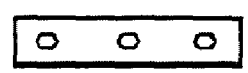
FIG. 6D

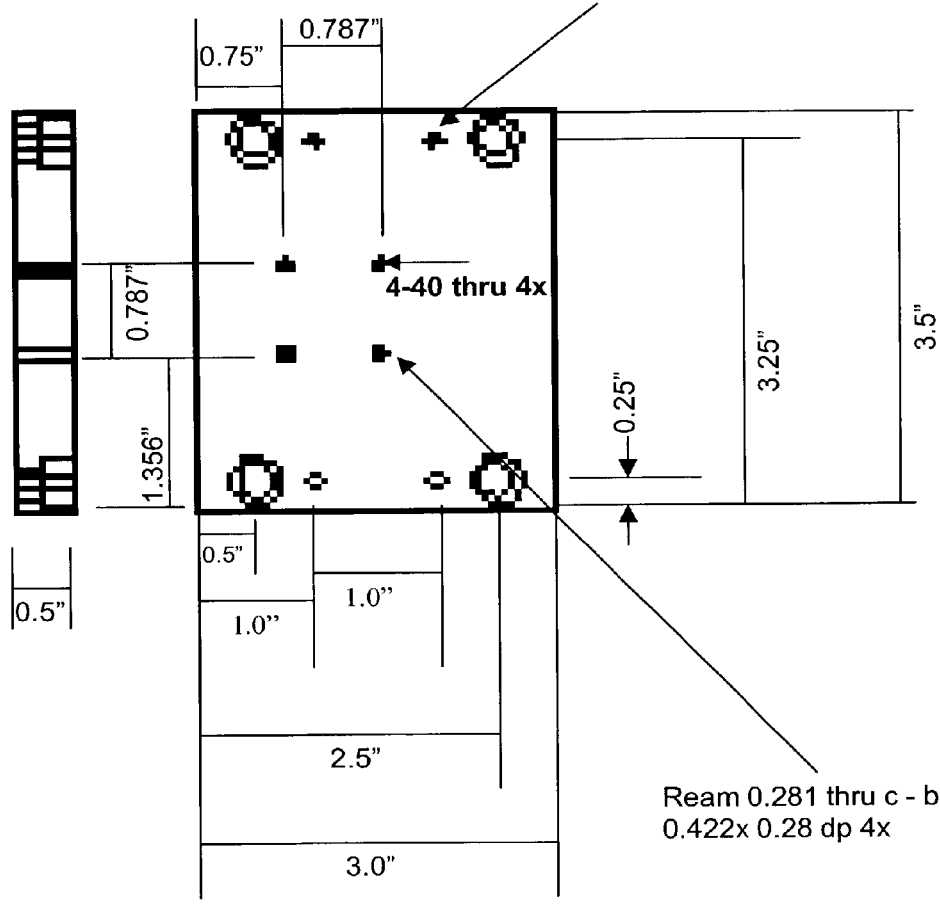

FIG. 9A
FIG. 9B
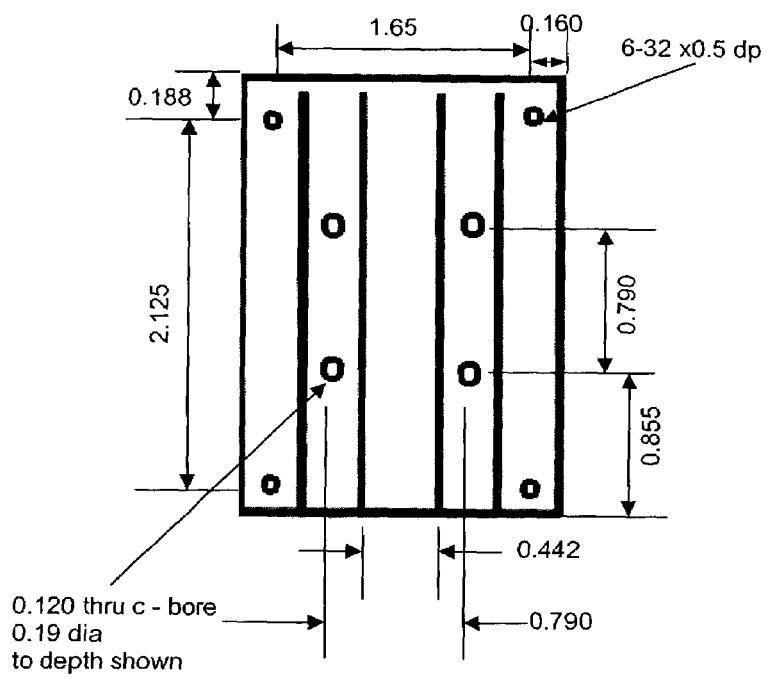
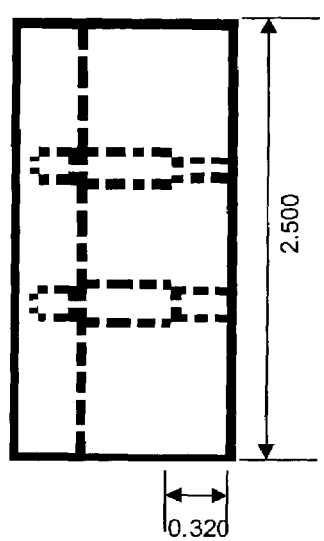
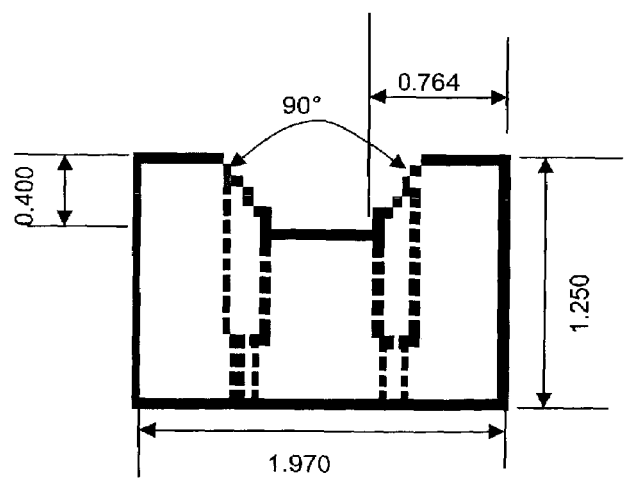
FIG. 9C 0.140 thru c- bore
0.250 diameter

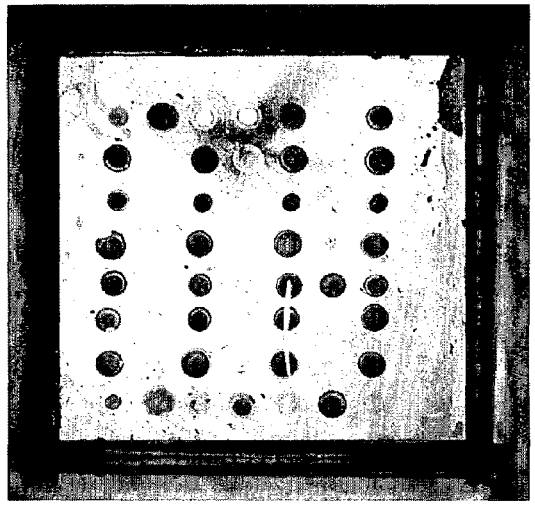
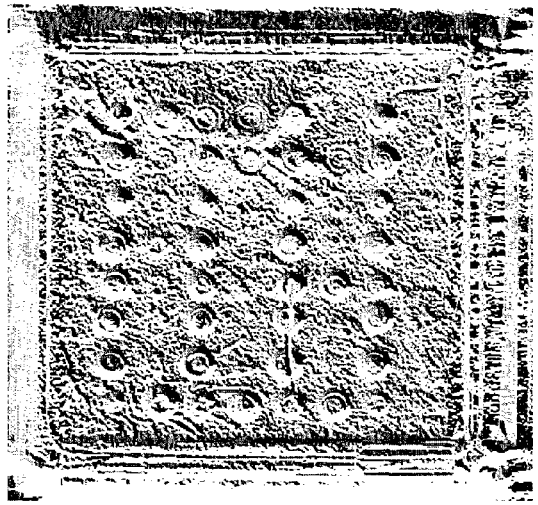
*FIG. 12A*                    *FIG. 12B*
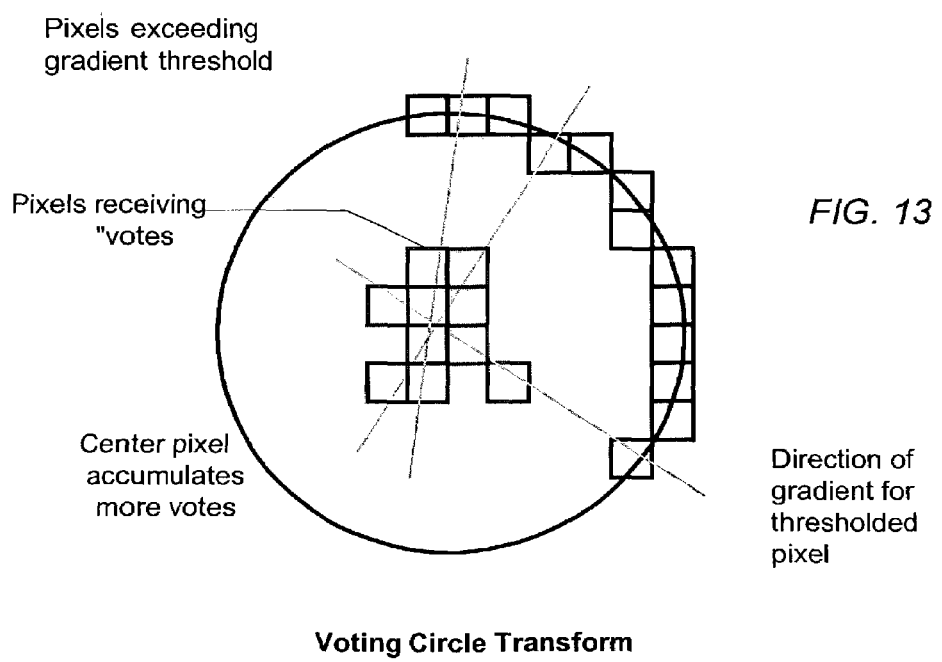
Voting Circle Transform
*FIG. 13*

DETECTION, RESOLUTION, AND IDENTIFICATION OF ARRAYED ELEMENTS

FIELD OF INVENTION

This invention relates to the optical detection, resolution, and identification of an array of elements, preferably for use on an optical thin film surface

BACKGROUND OF INVENTION

The following description of the background of the invention is provided simply as an aid in understanding the invention and is not admitted to describe or constitute prior art to the invention.

In the semiconductor field, films formed by vacuum evaporation, vapour deposition, spin coating or dip coating are commonly used at various stages of the semiconductor fabrication process. Control and monitoring of the actual thickness and physical properties of thin film layers is absolutely essential to the function of the devices created using this technology. These characteristics must often be monitored during and after fabrication. "Optical thin film determination" refers to methods for determining the thicknesss of one or multiple thin layer(s) formed on a substrate surface. Such "thin films" range from about 1 nm to about 100 µm in thickness.

Typically, optical thin film measurements rely on changes in one or more characteristics of light reflected from a substrate comprising an "optical thin film test surface." By this is meant that the surface is reflective of incident light, and is configured and arranged by selection of refractive index (n) and absorption coefficient (k) for generation of a signal directly due to a change in mass or thickness upon the surface. The signal is obtained by illuminating the surface with light; light is reflected from the surface or transmitted through the surface, and any thin film upon the surface will alter the color, ellipticity, and/or intensity of one or more wavelengths in the reflected or transmitted light due to an interference effect. This extent of the alteration, and hence the signal obtained, depends on the mass or thickness of any surface film(s).

Devices for optical measurement of thin films generally fall into two instrument classes: reflectometers and ellipsometers. Reflectometry is based upon measurement of changes in intensity and/or color of light reflected from the optical thin film test surface; ellipsometry is based on measurement of changes of the polarisation of light reflected from the optical thin film test surface. Such methods are well known in the art. See, e.g., Tompkins and McGahan, *Spectroscopic Ellipsometry and Reflectometry: A User's Guide*, John Wiley and Sons, 1999, which discusses the nature of optical constants of materials, instrumental aspects of reflectometers, ellipsometric spectra, and single-wavelength ellipsometry, as well as analytical approaches for collecting and analyzing ellipsometric and reflectance data.

Because of the ability of such methods and devices to sensitively detect changes in film thickness at molecular dimensions, the application of optical thin film measurements to biological systems has become well established. For example, devices and methods for direct detection of binding reactions (e.g., in immunoassay, nucleic acid hybridization, etc.) has been described. See, e.g., U.S. Pat. Nos. 6,483,585; 6,355,429; 6,287,783; 6,060,237; 5,955,377; 5,639,671; 5,631,171; 5,629,214; 5,552,272; 5,550,063; 5,494,829. While such methods do not depend upon the presence of a signal development element (e.g., a fluorometric, luminescent, or calorimetric moiety) for production of a signal, amplification methods (e.g., the catalytic production of a precipitate or the binding of particles such as latex, gold, etc.) to provide additional mass or optical thickness may be employed to enhance detection of the binding reaction.

SUMMARY OF THE INVENTION

The present invention relates to devices, compositions, and methods for manufacture and use of high-throughput thin film optical assay devices. The following sections describe hardware and software requirements for the analysis of optical thin film test surface arrays for use in medical or research applications such as genomics, proteomics, allergy panels, drug discovery, high throughput screening, pharmacogenomics, toxicogenomics, ADME screening, infectious disease panels, SNP (single nucleotide polymorphisms) analysis for a specific disease or condition, etc.

In a first aspect, the present invention relates to individual arrays that comprise a single optical thin film test surface that provides a plurality of discretely addressable locations, each comprising an immobilized capture reagent for an analyte of interest. These are referred to herein as "arrayed optical thin film test surfaces." Preferably, an individual arrayed optical thin film test surface comprises at least 4, more preferably at least 16, even more preferably at least 32, still more preferably at least 64, and most preferably 128 or more discretely addressable locations. One or more of the discretely addressable locations may provide control signals (e.g., for normalizing signals and/or that act as positive and/or negative controls) or fiducial signals (i.e., information that is used to determine the relative alignment of the arrayed optical thin film test surface within the device.

In a related aspect, the arrayed optical thin film test surfaces are contained in a larger "test surface carrier" that provides an "array of arrays" within a single housing, thereby further increasing the throughput Preferably, an individual test surface carrier comprises at least 1, more preferably at least 2, still more preferably at least 5, even more preferably at least 10, still more preferably at least 20, even more preferably at least 50, and most preferably at least 90 or more discrete arrayed optical thin film test surfaces within a single housing. Like the arrays, a test surface carrier may also be provided with fiducial locations that provide information that is used to determine the relative alignment of the optical thin film test surfaces within the test surface carrier.

The term "discrete" as used herein with regard to individual arrays refers to two or more arrays having discontinuous surfaces. The term "discretely addressable" as used herein with regard to individual locations on a single array refers to discrete areas of a surface from which a specific signal may be obtained.

Signal from discretely addressable locations on the arrayed optical thin film test surface is generated by a change in film thickness or mass as a result of a specific reaction of a target molecule with its corresponding capture reagent at a position within the array. As the film thickness or mass changes, light reflected from the surface undergoes a change in the polarization state, phase, or in interference color. Capture reagents may be small molecules, polypeptides, proteins, cyclic polypeptides, peptidomimetics, aptamers, antibodies, scFvs, polysaccharides, receptors, polynucleotides, and/or polynucleotide analogs; likewise, target molecules may be small molecules, polypeptides, proteins, cyclic polypeptides, peptidomimetics, aptamers, antibodies, scFvs, polysaccharides, receptors, polynucleotides, and/or polynucleotide analogs.

Any combination of materials with specific binding properties for one another may be used as capture reagent/analyte pairs in the present invention.

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "polypeptide" refers to a covalent assembly comprising at least two monomeric amino acid units linked to adjacent amino acid units by amide bonds. An "oligopeptide" is a polypeptide comprising a short amino acid sequence (i.e., greater than 2 to a few hundred amino acids). An oligopeptide is generally prepared by chemical synthesis or by fragmenting a larger polypeptide. Examples of polypeptide drugs include, but are not limited to, therapeutic antibodies, insulin, parathyroid hormone, polypeptide vaccines, and antibiotics such as vancomycin. Novel polypeptide drugs may be identified by, e.g., phage display methods.

As used herein, the term "antibody" refers to an immunoglobulin molecule obtained by in vitro or in vivo generation of an immunogenic response, and includes both polyclonal, monospecific and monoclonal antibodies, and antigen binding fragments thereof (e.g., Fab fragments). An "immunogenic response" is one that results in the production of antibodies directed to one or more antigens after the appropriate cells have been contacted with such antigens.

As used herein, the term "single-chain variable region fragment" or "scFv" refers to a variable, antigen-binding determinative region of a single antibody light chain and antibody heavy chain linked together by a covalent linkage having a length sufficient to allow the light and heavy chain portions to form an antigen binding site. Such a linker may be as short as a covalent bond; preferred linkers are from 2 to 50 amino acids, and more preferably from 5 to 25 amino acids.

As used herein, the term "polynucleotide" refers to a molecule comprising a covalent assembly of nucleotides linked typically by phosphodiester bonds through the 3' and 5' hydroxyls of adjacent ribose or deoxyribose units. An "oligonucleotide" is a polynucleotide comprising a short base sequence (i.e., greater than 2 to a few hundred nucleotides, with 25- to 50-nucleotide oligomers being common). Polynucleotides include both RNA and DNA, may assume three-dimensional shapes such as hammerheads, dumbbells, etc., and may be single or double stranded. Polynucleotide drugs can include ribozymes RNAi constructs, and polynucleotide vaccines. Polynucleotides may also comprise one or more substitutions, e.g., a ribose or deoxyribose substituted at the 2' and/or 3' position with -alkyl (e.g., —O-methyl, —O-ethyl, —O-propyl), -methoxyethoxy, -allyl, -amino, or -fluoro.

As used herein, the term "polynucleotide analog" refers to a molecule that mimics the structure and function of an polynucleotide, but which is not a covalent assembly of nucleotides linked by phosphodiester bonds. Peptide nucleic acids, comprising purine and pyrimidine bases linked via a backbone linkage of N-(2-aminoethyl)-glycine units, is an example of an oligonucleotide analog.

The term "polysaccharide" as used herein refers to a carbohydrate comprising 2 or more covalently-linked saccharide units. An "oligosaccharide" is a polysaccharide comprising a short saccharide sequence (i.e., greater than 2 to several thousand saccharide units).

As used herein, the term "cyclic polypeptide" refers to a molecule comprising a covalent assembly of monomeric amino acid units, each of which is linked to at least two adjacent amino acid units by amide bonds to form a macrocycle.

As used herein, the term "peptidomimetic" refers to a molecule that mimics the structure and function of a polypeptide, but which is not a covalent assembly of amino acids linked by amide bonds. A peptoid, which is a polymer of N-substituted glycine units, is an example of a peptidomimetic.

The term "aptamer" as used herein refers to polynucleotides that bind to non-polynucleotide target molecules (e.g., a polypeptide or small molecule).

A preferred arrayed optical thin film test surface is comprised of a substrate supporting an optical thin film test surface. Preferred substrate materials include materials that are substantially rigid, such as glass, rigid plastics, metals, silicon, etc. Particularly preferred substrate materials are described hereinafter. The substrate may inherently have a reflective surface to participate in the generation of the thin film effect to be measured, or may be modified to provide such a reflective surface, e.g., by vapour deposition of a metal layer. Alternatively, in various embodiments a transmissive substrate may be preferred. In various embodiments described hereinafter, the arrayed optical thin film test surface may further comprise one or more of the following additional layers placed upon the reflective surface: an anti-reflective layer; and an attachment layer providing a covalent or non-covalent linkage to immobilize the capture reagents. As described herein, each of these layers are optional, as an anti-reflective layer is not required in all modes of the invention; and the capture reagents may be directly immobilized to sites on the surface.

A preferred format is one that places individual arrayed optical thin film test surfaces into a device readily amenable to reagent delivery and assay manipulation, either manually or using off the shelf robotics. Thus, in various embodiments, 96-position plates providing spacing of individual array locations akin to that found in commercial 96-well plates are used to house a plurality of individual arrays for use in the methods and apparatuses described herein. It should be understood that additional plate configurations are within the scope of this invention, including multiples of 96 (e.g., 384 and 1536) wells, which are conveniently used with commercially available liquid handling robots.

In additional aspects, the invention relates to methods for constructing the arrayed optical thin film test surfaces and test surface carriers. As described hereinafter, the test surface carrier of the present invention provides advantages for a wide range of detection technologies beyond the optical thin film methods.

The methods and devices described herein are particularly useful for multiplexed detection of the presence or amount of a plurality of analytes in samples. The term "analyte" or "target" refers to any molecule being detected by an assay. The analyte (or target) is typically detected by immobilizing one or more binding partners (referred to herein as "capture reagents") at a test location on an arrayed optical thin film test surface. This binding partner immobilizes the analyte for detection by the methods described herein.

Preferred are biological samples. The term "biological sample" refers to a sample obtained from an organism. Such a sample may be obtained for the purpose of diagnosis, prognosis, or evaluation of a human in a clinical setting. In certain embodiments, such a sample may be obtained for the purpose of determining the outcome of an ongoing condition or the effect of a treatment regimen on a condition. Preferred biological samples are blood samples, tissue samples, stool samples, sputum samples, serum samples, plasma samples, cerebrospinal fluid samples, urine samples, and other fluids derived from a patient, organism, or sample.

In another aspect, the present invention also relates to methods, software and associated hardware, for manual to fully automated acquisition and processing of an image acquired from an array or array of arrays. While described herein in reference to analysis of arrayed optical thin film test surfaces, the skilled artisan will understand that these methods, software, and hardware are applicable to the analysis of arrays generally, including tissue arrays (e.g., MAXAR-RAY™ commercially available from Xymed); nucleic acid arrays and microarrays (e.g., GENECHIP® commercially available from Affymetrix); protein/nucleic acid arrays and microarrays (e.g., commercially available from Panomics); antibody arrays and microarrays (e.g., commercially available from Clontech); and protein arrays and microarrays (e.g., commercially available from Ciphergen).

In preferred embodiments, an integrated "image analysis station," is provided which comprises one or more, and preferably all, of the following elements: a test surface carrier comprising a plurality of arrays as described herein; optical components for illuminating the array(s) for generation of a signal from a plurality of discretely addressable locations; the optical components comprise a diffuse light source; a digital camera for recording images of one or more arrays; optical components for focus and/or frame control of the digital camera; a stage for movement of the test surface carrier relative to the field of view of the digital camera; stage movement mechanism; a manual control for the stage movement mechanism; a manual control for the digital camera; a computer processor integrated with the stage movement mechanism and/or the digital camera; software providing instructions for predetermined stage movement and/or camera control; a digital storage medium for recording of images and results; and/or a user interface for inputting commands and/or viewing images and/or results. In preferred embodiments, image analysis is performed automatically for all reacted arrays within the test surface carrier with no user intervention.

The terms "image analysis" and "image processing" as used herein refer to acquisition of one or more digital images from an array, and the use of the image(s) collected to determine the presence or amount of one or more analytes at one, and preferably at a plurality, of discretely addressable locations on the array.

The term "optical components for illuminating the array" as used herein refers to a light source and associated optical elements for providing the desired incident light on an array. Depending on the assay format, the optical components for illuminating the array may simply be a white light or a coherent light source; or may include a filter between the light source and the array to remove undesired light wavelengths (e.g., a low-pass, high-pass, or band-pass filter); a polarizer between the light source and the array to alter the polarization state of the light; and/or other components commonly used by the artisan in reflectometry and/or ellipsometry. Ellipsometric methods may require the use of a coherent and/or monochromatic light source.

The term "diffuse light source" as used herein refers to a light source providing substantially even illumination across the field of view of the digital camera.

The term "digital camera" as used herein refers to a camera that provides a digital output signal corresponding to an image obtained by the camera. Suitable cameras, including CMOS (Complementary Metal Oxide Semiconductor, APS (active pixel sensor), CCD, and non-CCD cameras, are well known in the art. Preferred types of CCD cameras are Linear, Interline, Full-Frame, and Frame-Transfer. A Linear CCD consists of a single row of pixels; to define an image, a Linear CCD must be scanned across the plane of the image, building the picture row by row. Interline, Full-Frame, and Frame-Transfer designs are considered Area Array CCDs, because they are composed of multiple rows and columns forming a rectangular or square area. In an Interline CCD, each pixel has both a photodetector and a charge storage area. The storage area is formed by shielding or masking part of the pixel from light and using it only for the charge transfer process. Full-Frame CCDs devote the entire pixel to image capture. Therefore, when the charge transfer occurs, the pixel is busy and cannot continue to capture photons. To keep the pixels from continuing to read additional light when they are involved in charge transfer (which can lead to light smear on the image), a mechanical shutter between or behind the camera lens is often employed. Finally, Frame-Transfer CCDs are similar to Full-Frame, but they mask out half of the array to provide temporary storage for the electric charges, referred to as the "storage array". Analog cameras coupled to an analog-to-digital converter are also within the scope of the term, as such cameras provide the required digital output of images for further processing by a computer processor.

An image is said to be "recorded" by a camera if the image is acquired for processing by a computer processor. As described herein all or a portion of the image may be stored (either temporarily or permanently) within the camera electronics, or may be transferred to an attached digital storage device, or may be directly transferred to the computer processor without storage. Images may be acquired as a single test surface at a time or as multiple test surfaces within a single image, as static images or real time images, or as continuous or scanning mode images, depending on the requirements of a particular device and/or the throughput requirements.

The term "optical components for focus control" as used herein refers to optics and associated mechanical hardware employed to bring an area of interest into focus for recording by a digital camera. Similarly, "optical components for frame control" refers to optics and associated hardware employed to provide zoom and pan control to the digital camera.

The term "stage" as used herein refers to mechanical hardware required to support and provide movement along one or more axes of a test surface carrier. Preferably, a stage provides movement along orthogonal axes arbitrarily labeled X and Y; and in certain embodiments includes movement along a Z (perpendicular to the X/Y plane) axis.

The term "stage movement mechanism" as used herein refers to components (e.g., stepper motors, gearing, rack and pinion elements, bearings, etc.) providing movement to the stage.

A manual control or computer processor is "integrated" with an element of the device if instructions may be relayed from the manual control or computer processor to the element, providing a subsequent action by the element. Preferably, this integration also provides feedback from the device to the manual control or computer processor. For example, a digital camera that is integrated with a computer processor may receive instructions from the processor to record an image, and/or all or a portion of the image data may be transferred from the camera to the processor. Integration may be provided in a wired fashion (e.g., via hard wiring, a serial port (such as a standard RS-232 port), a USB port, a "fire wire" port, etc.) or wireless fashion (e.g., connected via an infrared connection, a radio frequency connection, a Bluetooth® connection, etc.).

The term "software" as used herein refers to a set of instructions, programs, and/or procedures stored in a volatile or non-volatile digital medium, for execution by a computer processor. Such software may be stored on hard or floppy disks, in volatile or non-volatile memory, on optical media, etc. In the present invention, software may provide instructions for performance of an assay, e.g., by robotic systems; for recording of digital images; and/or for analysis of digital images as described hereinafter.

The term "computer processor" refers to a digital device for performing the logic operations of a computer's program, often referred to as a "CPU." Typically, a computer processor comprises a datapath having an arithmetic logic unit (ALU) that performs arithmetic/logic operations, an address generation unit to provide memory addresses, and a control unit to provide the proper control signals for the various devices of the datapath to perform the desired operation(s). Computers typically have a processor, a main memory, a secondary storage device, and a bus for connecting the processor, the main memory and peripheral devices. Digital cameras may be connected to the computer via this bus, or via parallel or serial ports. Any of a number of well known computer processors, such as processors from Intel Corporation, of Santa Clara, Calif., may be used in the devices described herein.

The term "digital storage medium" as used herein refers to any medium in which information is stored in digital form. These include hard and floppy disks, optical disks, random access memory, read only memory, etc.

The term "user interface" as used herein refers to an element allowing user interaction with the device of the present invention, including one or more of the following: keyboards, mice, joysticks, keypads, touchscreens, monitors, etc.

Except as otherwise noted, the term "about" as used herein refers to +/−10% of any given measurement.

While the hardware of the image analysis station described herein is described in terms of the detection of thin film changes, the skilled artisan will understand that various components, including in particular the software, could be used in conjunction with any image analysis method regardless of the method of signal generation. The image merely needs to provide signals that contrast the background and possess some spatial resolution of the elements within the array that can be stored in an appropriate processing format. Thus the software is compatible with fluorescence, chemiluminescence, and other chromophores. Thus, in one aspect, the present invention relates to methods and devices, including software, for automated image analysis to determine the presence or amount of one or more analytes at one, and preferably at a plurality, of discretely addressable locations on an array.

As described herein, the image analysis instruments of the present invention preferably analyze a large number of arrays with limited user input and no user location of the array, most preferably in a completely automated manner. But manual sequences can still be performed if required or desired. The image analysis station has been selected to read a highly reflective test surface that generates signal in the reflected light from the interaction of light with a thin film generated on the surface. The thin film properties of the surface are permanent records of the reaction and can be analyzed as many times as required. The signal generated is not susceptible to photo-bleaching or photodecay and thus is stable throughout the analysis procedure. As the thin film effect is inherent in the layers of the device, there is no cross-talk between reacted zones such as can be observed when measuring fluorescence or other chromophores.

To facilitate ease of use, the image analysis station is designed to analyze surfaces that are mounted in the bottom of a depression, such as in a microtiter well. This provides an easy mechanism to manipulate and deliver samples and reagents but requires that the image analysis station reproducibly locate each well and then be capable of focusing into the well to acquire the image without interference from the walls of the wells. The same optical configuration can be used to analyze surfaces presented in a wide variety of other delivery formats including a simple slide format or individual test surfaces. The stage preferably is adaptable to hold each type of format and appropriately move the test surfaces to image each array in the device.

The test surface carrier described in the following preferred embodiments provides square wells to receive the manufactured test surfaces that are coated with an array of biological capture reagents. While commercially available microtiter plates can serve as the template for the construction of the test surface carrier, an improved plate designed for this specific application is described. This microtiter format plate design could be used to deliver any type of test surface desired but is particularly well suited for use with optical thin film surfaces. Optical thin film surfaces may be analyzed through upper surface reflection or for transmission measurements depending on the design of the optical support or surface and the optical path of the detection system. The signal generated is a function of the test surface used. For example a glass support may be used in combination with a fluorescent or chemilluminscent tag or marker. Measurements may be made in the reflectance or transmission mode. The improved test surface carrier or microtiter plate maintains the footprint of existing microtiter plates and thus is compatible with all of the off the shelf, automated, sample processing equipment. Thus the improved test surface carrier is suited to high throughput applications.

Once an array is reacted, and regardless of the method of signal generation, various image analysis tools typically employed by the artisan require the user to define or locate the position of the array, the number of elements in the array, and the location of the elements within the array. This is generally accomplished by requiring the user to select an array size and generating a grid that matches the selected parameters. The user then must drag the grid over an image of the reacted array and ensure that each grid element corresponds to an appropriate array element. Thus the user can account for any skew or stagger or mis-alignment of elements within the array. While performance of these existing tools is well suited to analysis of single arrays, even with a large number of elements, they are not well suited to analysis of large numbers of arrays, of even a limited number of elements, with any frequency of analysis. The new "spot finding" methods, provided as software or as general or special purpose computers programmed to perform the required steps of this invention, advantageously address moderate to high throughput applications.

The summary of the invention described above is not limiting and other features and advantages of the invention will be apparent from the following detailed description of the preferred embodiments, as well as from the claims.

BRIEF DESCRIPTION OF THE DRAWINGS

FIG. 3 illustrates the assembly of optical path components for an image analysis instrument according to an embodiment;

FIGS. 5A-5D and 6A-6D illustrate embodiments of side support brackets for the image analysis instrument;

FIGS. 8A-8B illustrate an embodiment of a camera support plate for the image analysis instrument;

FIGS. 9A-9C illustrate an embodiment of an extension tube bracket for the image analysis instrument;

FIGS. 12A-12B illustrate gradients in an array of spots;

FIG. 13 illustrates a voting circle transform for gradient magnitudes and directions;

DETAILED DESCRIPTION

Figure 1:
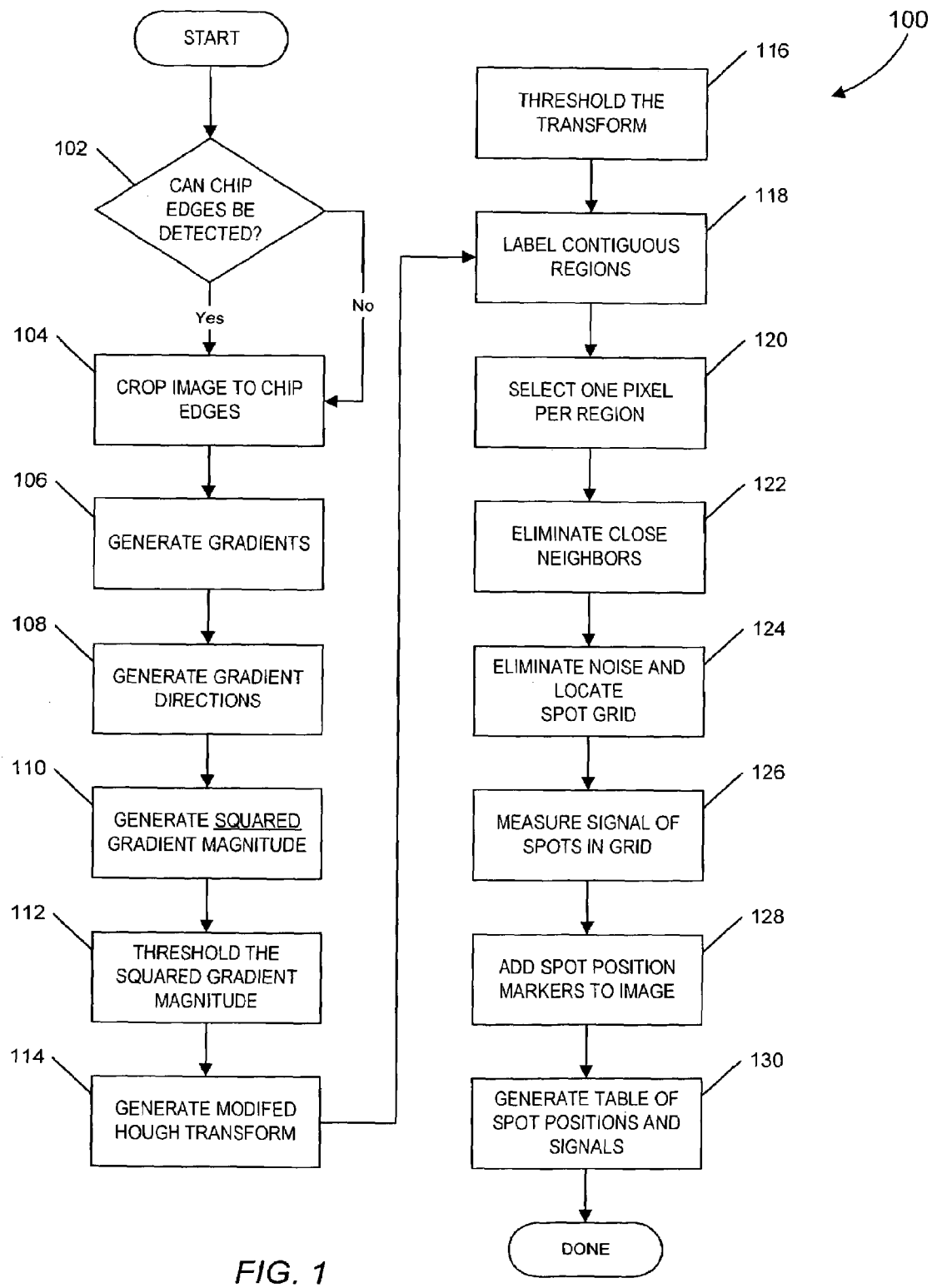
FIG. 1 is a flow chart illustrating one embodiment of a method for generating a table of spot positions and intensities.
Figure 2A:
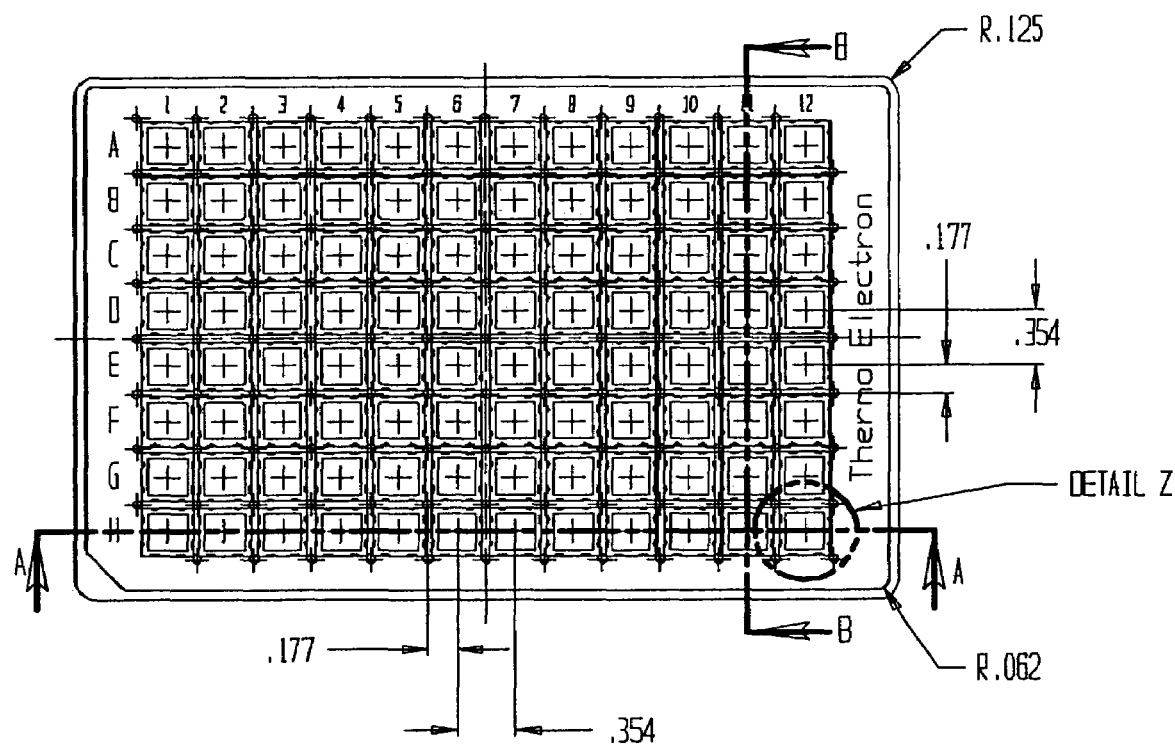
FIGS. 2A-2F illustrate one embodiment of a test surface carrier according to the present invention.
Figure 2B:
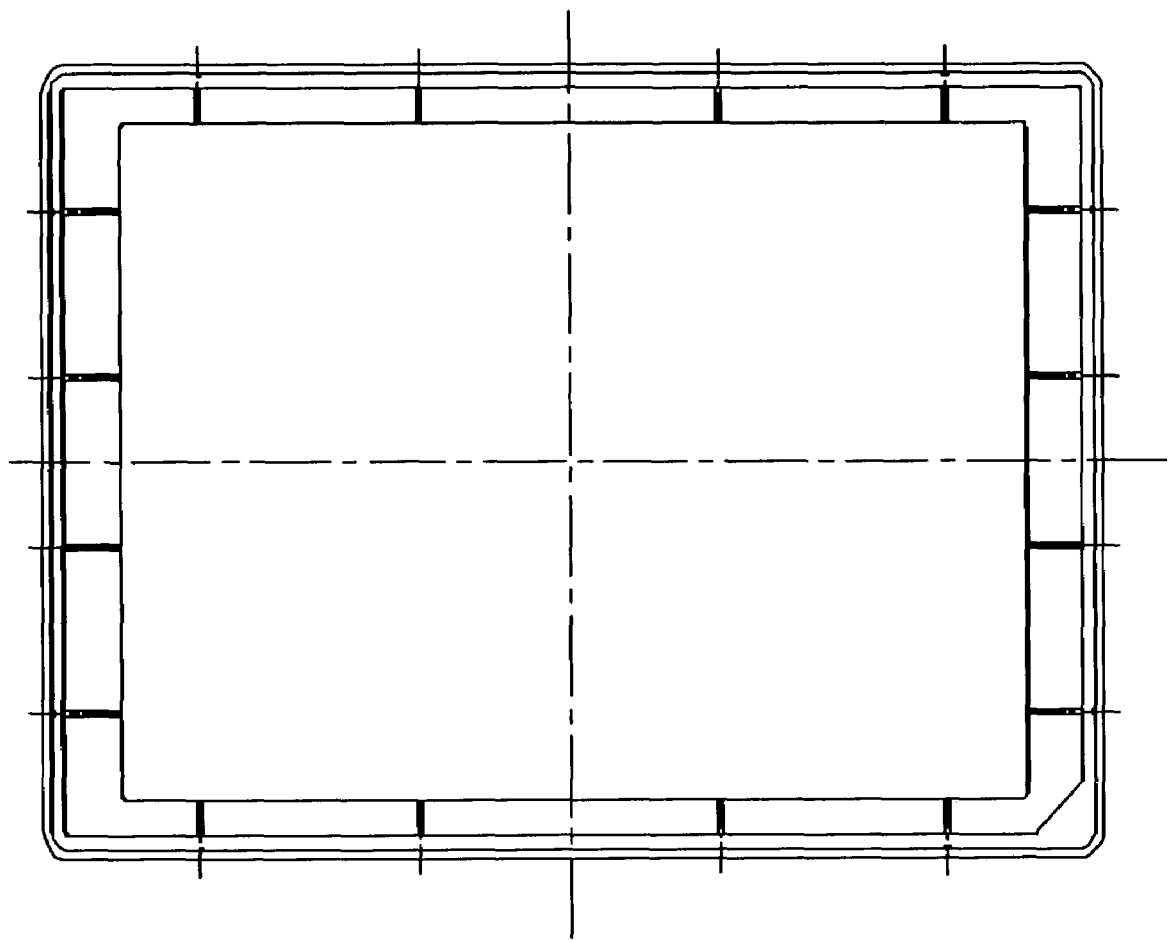
Figure 2C:
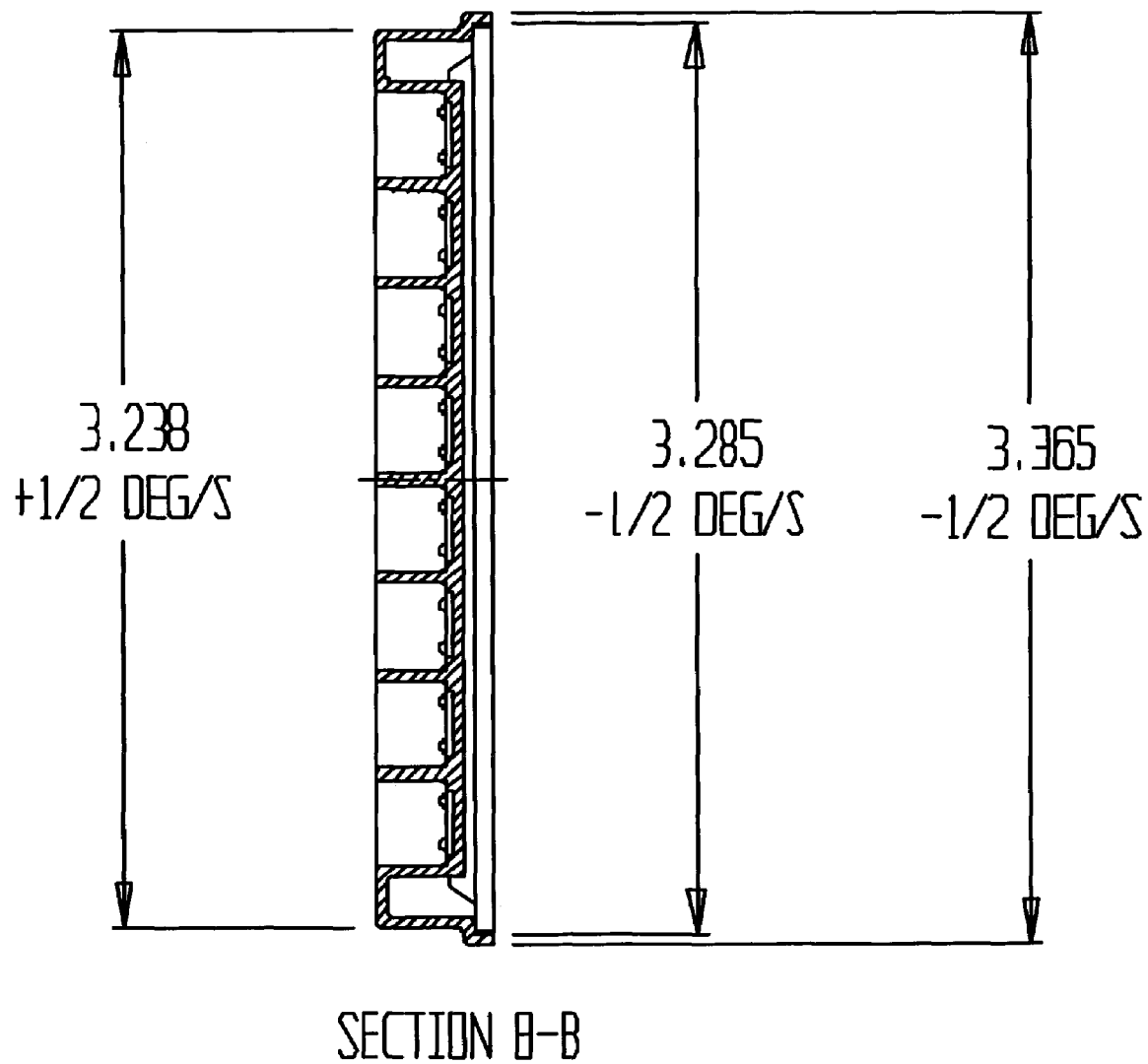
Figure 2D:
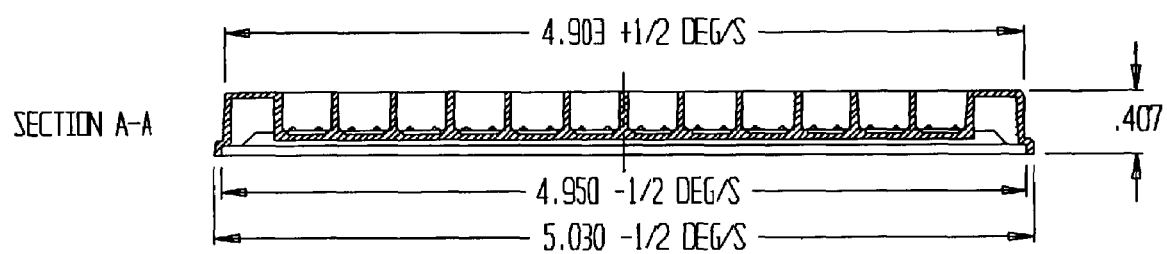
Figure 2E:
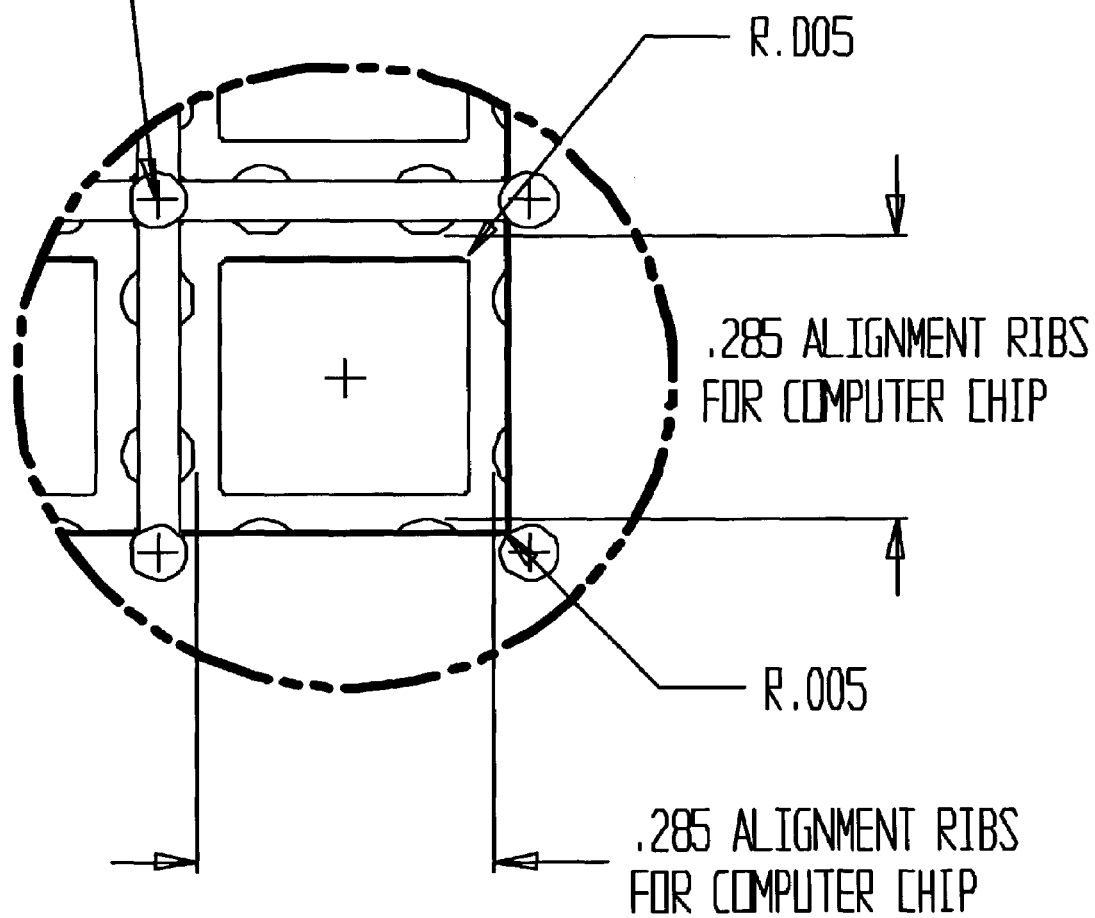
Figure 2F:
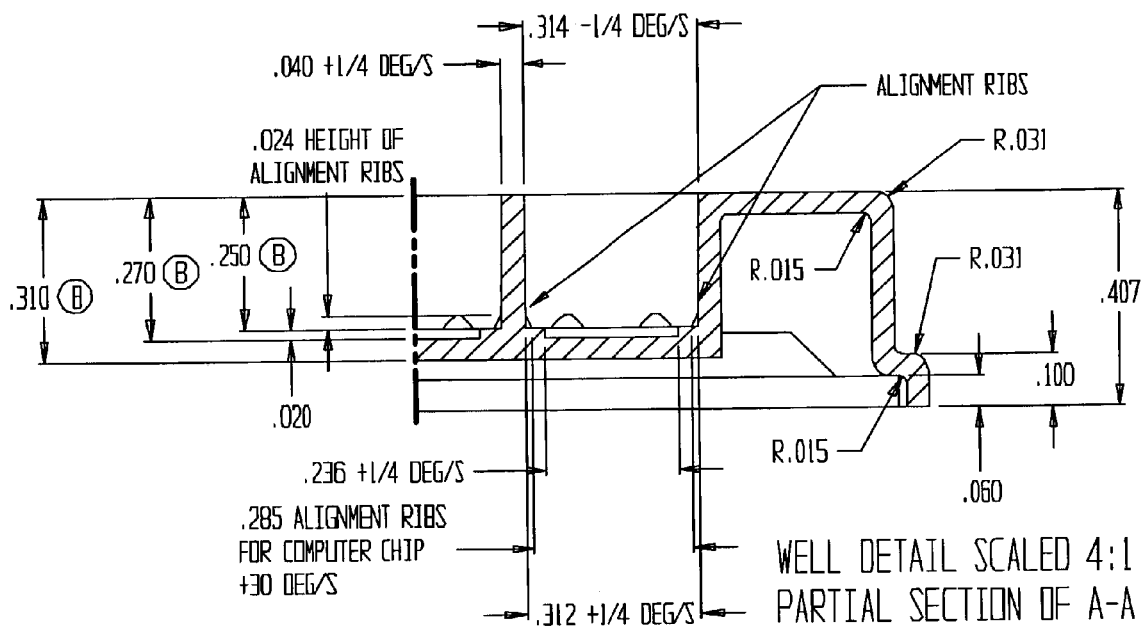

As discussed above, the present invention is described in reference to analysis of arrayed optical thin film test surfaces. The skilled artisan will understand that these methods, software, and hardware are applicable to the analysis of arrays generally. For thin film imaging, the image analysis station includes one or more, and preferably each, of the following: an optical test device; a CCD camera; a coaxial diffuse light source; an optional polarizer; an extension tube; focusing lens; optional auto-zoom and auto-focus capability; an x, y stage (with or without closed loop positional control); support structures; an instrument housing; a light power source; a stage controller; a joystick for manual stage control; a computer or equivalent for software and hardware control; a user interface; a monitor; and software.

The test surface carrier is a formatting device designed to deliver the arrayed optical thin film test surface(s), each comprising a patterned array of discrete capture locations, provide for reagent delivery and assay processing, and include a surface that will seat into the x, y stage in a stable fashion. The delivery platform can be in the shape of a standard microscope slide or configured as a standard microtiter plate of any well number. The preferred embodiment uses square wells to receive the test surface. The test surface carrier can be used to deliver test surfaces for non-thin film applications.

The optical thin film test surface may be cut, scribed, or otherwise broken into appropriate dimensions, and then glued or fused into the test surface carrier. The test surface carrier may hold one or more optical thin film test surfaces depending on the configuration of the test surface carrier. A preferred configuration for the test surface carrier is a 96 well microtiter plate having well spacings that correspond to common commercially-available microtiter plates. In the preferred embodiments, each well contains a 7 mm×7 mm optical thin film test surface; thus, preferably the wells in the plate are square. If other optical thin film test surface configurations are used (e.g., rectangular, circular, etc., each well may be designed appropriately to accommodate the test surface. When the microtiter plate is used to deliver test surfaces to an analytical method regardless of method of signal generation the individual array surfaces should be processed to a size that is appropriate for the dimension of the test surface carrier.

If a microscope slide is the test surface carrier then a single 1"×3" test surface may be mounted in the test device or a number of smaller strips or squares may be mounted into the test carrier that retains the 1"×3" size.

Regardless of the assay format or detection means used, test surfaces are prepared by immobilizing an array of capture reagents on the test surface. The capture reagents can be a complex combination of materials designed to interrogate a sample for a range of different analytes, genes, gene products, genomic DNA, small molecules, SNPS, or other materials of interest. Each capture reagent can specifically capture a target nucleic acid sequence, protein, sugar, lipid, hormone, or other analyte. As an example the capture reagents could be antibodies specific to a range of cytokines in a sample. Or the capture reagents could be a set of oligonucleotides that are specific to a combination of genes that are markers or indications of a specific disease. Or the capture reagents could be a set of oligonucleotides that are specific to SNP mutations in a specific gene that indicate the carrier status of an individual for a given disease, like cystic fibrosis (CF). Or the capture reagents can be antibodies specific to a panel of allergans for allergy screening, or specific to bacterial and/or viral antigens (or oligonucleotides for genes) for differential diagnosis of the caustive agent of infections like a respiratory infection.

The software designed for the image analysis of individual arrays automatically identifies and verifies the location and signal strength for each test element in the array. To automatically process the array, the preferred embodiment first locates the edges of the test surface in the image if possible. If the edges are found, the area of the image outside of the edges is eliminated from further consideration. Next, any possible features of the correct size, shape and intensity are located in the image. The number of such features is counted. The count of such features is used to determine the type of sample in the image. For example, a reacted patient sample would have a feature count within a certain range; a blank would have a different range; an empty well would have yet another typical range for the count. Once the type of sample has been determined, a set of heuristic rules is applied to eliminate spurious noise features. For example, a spot within a small number of pixels of the test surface edge is more likely to be due to washing problems than actual reactions and may be eliminated from further consideration. Next, the algorithm attempts to locate the grid structure from the remaining spot locations. A clustering algorithm and additional heuristics may be applied to define the location of the rows and columns of the spot grid. Rows and columns containing few or no reacted zones may have their positions estimated from the positions and spacings of other rows and columns containing more spots. Finally, spots are matched to locations in the grid and signals are measured. A table of spot positions and signal strengths is generated for further classification. The software and the test surface carrier to be described are generally suited for use in non-thin film applications as well. One embodiment of a method for generating the table for spot positions and signals is described below with reference to FIG. 1.

Software requirements for the system include an image acquisition protocol, stage movement and positional control, array identification, array element identification, array element quantification, array corrections for skew, production of a results table by array element, background acquisition, background correction, data processing and interpretation, and result reporting. A number of commercial sources for image acquisition and stage control are available. The suppliers of CCD cameras and the stages also provide software that can be used for these functions and then integrated into a final software package. Scanalytics provides an image analysis package that integrates image acquisition and stage control with other software protocols for the collection and analysis of an imaged array. However, this software requires a large amount of user interaction to analyze even small arrays.

Test Surface Design

Methods for the design of optical thin film test surfaces for use in optical thin film assays are well known in the art. See, e.g., U.S. Pat. No. 5,629,214, which is hereby incorporated in its entirety, including all tables, figures and claims. A wide range of rigid materials may form the substrate, including glass, fused silica, plastic, ceramic, metal, and semiconductor materials. The substrate may be of any thickness desired. Flexible optical substrates include thin sheets of plastic and like materials. Most substrates require only a standard solvent, plasma etching, or acid cleaning, well known to those skilled in the art, before subsequent layers may be deposited on them.

The optical thin film test surface is generally a reflective surface, preferably silicon or a silicon coated substrate material. For use in a reflection-based assay the major requirement in selecting an substrate is that the reflection occur, or be made to occur, only at the upper surface. The surfaces of many solid materials, such as glass, and semiconductor materials, such as silicon, metals, etc., are sufficiently smooth to provide specular reflection if they are polished. Provision of a reflective surface may also be easily accomplished by vapor deposition of a thin metal film on the substrate, and attachment of subsequent layers may also be provided by techniques known to those skilled in the art. For example, the uppermost surface of a glass substrate may be coated with a layer to prevent unwanted reflections from the lower surface.

A reflective surface is desired to allow the application of an anti-reflective (AR) film stack on the support material. The use of an AR layer may also be appropriate for use in a transmission mode of detection, provided that the underlying substrate is transmissive. An anti-reflective film stack allows signal generation through destructive interference as the film thickness on the optical test surface changes. Typically, the substrate (glass, quartz, etc.) is coated with a thin layer of material so that reflections from the outer surface of the film and the outer surface of the substrate cancel each other by destructive interference. Two requirements create an exact cancellation of reflected beams with a single-layer coating: The reflections are exactly 180 degrees (pi radians) out of phase, and they have the same intensity. The thickness of a single-layer antireflection film should be an odd number of quarter wavelengths in order to achieve the correct phase for cancellation. Where three or more reflecting surfaces are involved, complete cancellation can be achieved by carefully choosing arbitrary phase and relative intensities. This is the basis of a two-layer antireflection coating, where the layers are adjusted to suit the refractive index of available materials, instead of vice versa. For a given combination of materials, there are usually two combinations of layer thicknesses that will give zero reflectance at the design wavelength. Many optical systems (particularly imaging systems) use polychromatic (more than one wavelength) light. In order for the system to have a flat spectral response, transmitting optics are coated with a broadband or dichroic antireflection coating.

Destructive interference of light reflected, or transmitted, from the optical test surface can be detected with a digital (e.g., CCD) camera as a change in color or when using a gray scale camera as a change in gray scale value. A reflective surface is also suited to ellipsometric-like analysis in the absence of an anti-reflective film stack but this may require an additional polarizing element on the detection side of the optical path. In this case the thin films on the reflective optical support can be used to generate phase changes in the incident light that are measured as a change in intensity of the reflected or transmitted light directly at the detector.

A common anti-reflective film stack would be to coat a silicon substrate with a layer of silicon nitride. This stack is anti-reflective to the blue wavelengths and generates a gold background. When the thickness of the surface is changed by capture of a target molecule then the anti-reflected wavelengths are shifted and a purple-blue color is generated.

Once an optical thin film test surface has been provided, consideration must be given to attachment of capture reagents, such as small molecules, polypeptides, proteins, cyclic polypeptides, peptidomimetics, aptamers, antibodies, scFvs, polysaccharides, receptors, polynucleotides, and/or polynucleotide analogs. Methods for attachment of molecules to surfaces, e.g., by covalent attachment, electrostatic attachment, hydrophobic attachment, etc., are well known in the art. Such materials may be attached directly to the optical thin film test surface if sufficient sites are available for binding of the capture reagent in an amount sufficient to provide a signal in the optical assay. Preferably, an attachment layer may be interposed between the optical thin film test surface and the capture reagent. An attachment layer may be employed, for example, to extend the capture reagent from the surface for efficient binding. In addition, attachment layers formed from a polyvalent molecule, such as the group consisting of dendrimers, star polymers, molecular self-assembling polymers, polymeric siloxanes, and film forming latexes, may be employed to amplify the number of binding sites on the optical thin film test surface.

For an optical thin film device, surfaces are preferably processed as follows. For clarity an AR coated surface will be described but the AR layer is optional. An AR layer is generally required for visual analysis, calorimetric analysis, or grayscale imaging. Monitoring a change in ellipticity does not require the presence of an AR layer. A silicon wafer (diameter is not critical) is coated by a vapor deposition process with a layer of silicon nitride. The thickness and refractive index are selected to match the application. A preferred setting is a 500 Π±15Π thickness and a refractive index of 1.985±0.015. Other AR materials are appropriate and known to those skilled in the art.

The AR coated wafer is coated in a spin coating process with a layer of a branched siloxane. Siloxanes are the preferred attachment layer coating but other chemical modifications of the surface are possible. Next a layer of a long chain amino acid (polyphenylalanine-polylysine) is coated onto the siloxane layer by a solution coating process. The polyphenylalanine-polylysine surface provides a layer of amines for the covalent attachment of an array of capture reagents, together with a sufficiently hydrophobic character for attachment to the siloxinated surface. If covalent attachment is not required, as for many protein based capture reagents, then this layer may not be required. Surfaces that do not require a high degree of surface manipulation, assay stringency, or washing may be fine with a passive adhesion of the capture reagent. Other surface modifications for different covalent attachment schemes are known to those skilled in the art. Amines can be activated by a number of chemical reagents that are subsequently reactive with another amine. The surface amines may be activated or amines on the capture reagent may be activated. The activated amines are then reacted with the corresponding unmodified amine. Other chemistries include the use of thiols, aldehydes, imidoesters, hydrazine, isocyanates, etc as reactive groups.

Array Production

Test surfaces can be spotted with arrays of varying density. The number of spots in an individual array will depend on the analysis to be performed. Multiple replicates of the same array can be applied to discrete sections of the test surface and may or may not rely on some type of physical barrier to separate the individual arrays on the production surface. Or multiple arrays of unique content (each with a number of elements in the array) may be applied to the test surface. Again some sort of physical barrier may be used to separate the individual arrays.

For some applications it may be desirable to provide multiple copies in the array of a specific capture reagent. For example when an SNP has a high frequency in the population to be screened for a genetic trait it may be appropriate to build in multiple copies of the two capture probes for that SNP. Or a capture reagent specific to a particularly pathogenic organism or strain of organism may merit additional copies in the array. Thus, critical elements in the array can be easily verified in a single analysis. In addition to capture reagents specific to the analyte or disease profile to be examined, control reagents and orientation reagents may be provided within the array.

One of the key considerations in the design of the capture reagent layout for each application is the number of signals that will routinely be generated in each column or row of the array. This design element is important for the automated array identification algorithm to be described below. Sufficient elements in each column and row must generate signal to provide optimal and quick identification of each column and row during processing of the acquired image.

The design and screening of the capture reagents for the array involve many factors. All of the capture probes immobilized within the array must work under common reaction conditions while maintaining the sensitivity and specificity required from the finished test surface. Thus spotting reagents must be designed to provide a similar surface tension for uniform spot size production on the test surface. The spotting reagent should also provide a surface tension (in conjunction with the surface chemistry, if any) that maintains each capture reagent as a discrete and unique zone within the array. But they must also provide for an environment that promotes the adhesion of the specific capture reagent to the surface or maximizes the chemistry of attachment utilized. The spotting reagent may also be required to prevent drying of an extremely small volume of spotted capture reagent during the surface reaction immobilization time.

Capture reagents may be applied as discrete spots with a number of different spotting technologies. If the spotting technology allows, and depending on the number of array elements to be generated, all of the capture reagents that compose an array can be applied simultaneously to the test surface. The spotting head or the test surface is then indexed to a new position and the next array generated. Alternatively, each capture reagent can be applied to a specific position on the test surface individually and sequentially until the complete array is generated. For ease of production, it is preferred that the capture reagents be applied to a bulk test surface where a number of arrays (dependent on the bulk test surface size) can be generated in simultaneous or sequential fashion. Once the capture reagents are immobilized onto the bulk test surface it can then be processed into a number of discrete arrays for immobilization within the test surface carrier. For example a 4 inch silicon wafer broken into 7 mm$^2$ test pieces can yield about 124 arrays.

In preparing an arrayed optical thin film test surface using array spotting technologies, care must be taken to avoid abrasion of the surface, as deviations in the surface profile of the final array may be observed as a background signal or as spurious test locations in the assay. Selection of the array spotting method employed must balance the need to deliver the required capture reagents to an (often hydrophobic) optical surface, and the need to avoid damage to the optical stack.

Certain discrete locations on the array may also be maintained for purposes of positive and negative controls, signal intensity standards, and "fiducial spots." In the latter case, the skilled artisan will understand that the capture locations on an unreacted array will be undetectable to the assay, assuming the background signal from the array spotting method is minimized. If one assumes a 16-spot 4×4 array, each corner spot will also be indistinguishable from any other corner spot; thus, determining the proper "upper left" location of the array may be impossible. One or more predetermined locations on an array and that are observable in an unreacted state may be used to determine the relative orientation of the capture locations, either during further manufacturing or during image analysis.

Once all of the arrays are generated on a bulk or production level test surface additional processing may be required. This includes incubations, wash and dry processes, overcoating processes for stability or to reduce nonspecific binding. All of these processes occur before cutting, scribing, laser cutting, or other methods of breaking the bulk test surface into appropriate test surface size for incorporation into the test surface carrier. For certain applications the test surface construction might occur directly on the lower surface of the test surface carrier. When multiple copies of individual arrays are generated on a bulk test surface part of the array design must include sufficient surrounding area for a separation process to cut or otherwise separate individual arrays without damaging the array. This outer edge of the individual test surface is also important for the placement equipment that mounts the test surface into the test surface carrier. This is a contact point for that equipment. Once completed individual test surfaces are generated they must be placed into the test surface carrier. Some form of adhesion of the test surface to the carrier is required. This may be accomplished with a glue, a heat seal, chemical weld, or other technique as appropriately addresses the composition of the test surface, the carrier, and the capture reagent stability and sensitivity to processing. The individual test surfaces must be inserted into the carrier with the proper orientation, limited amount of tilt (flatness), and a limited amount of skew.

In the present invention, obtaining the necessary flatness in the test surface carrier preferably requires placing each array into the carrier with a tilt tolerance of +/−about 10° relative to the horizontal plane, more preferably +/−about 5° relative to the horizontal plane, and most preferably +/−about 10 relative to the horizontal plane.

The number of capture reagents used in the array is determined based on the analytical requirements of the test to be performed, the size of the test surface in the format selected, and the size of the spots of capture reagent applied. As an example, an array of at least 59 oligonucleotides is desired to analyze a patient sample for SNP mutations (25 mutations and 6 polymorphisms) in the CFTR gene for cystic fibrosis. For the 25 mutations and 3 of the polymorphisms a pair of capture probes are spotted. One of the capture probes is specific to the wild type sequence and one is to the mutant sequence of the gene at the specific SNP position to be analyzed. Three of the polymorphisms require a single capture probe. The panel of mutations to be detected is based on a recommendation from the American College of Medical Genetics.

Test Surface Carrier Design and Production

While commercially available square well 96 well plates can be used as a test surface carrier, dramatic improvements in device performance and production yields can be obtained with a newly designed carrier. This carrier maintains the 96 well format as the equipment available for processing this format is widely available. See FIGS. 2A-2F. The improved test surface carrier maintains the overall exterior dimensions of a standard 96 well plate so that it is still compatible with all of the robotics designed to work with a 96 well plate. See FIGS. 2A through 2D.

To improve the placement and orientation of the test surface, the well wall height has been decreased so the reagent volume required to fill a well is decreased from 650 µl to 320 µl. This reduces the depth that robotics must accommodate to place the test surface within the well and potentially reduces imaging artifacts from the shadowing obtained from the well walls. The reduction in the volume of reagent that can be applied to a test surface should not have significant impact on assay performance but could have a positive impact on reagent costs during the assay protocol. Also the shallower well design may serve to improve the washing steps in the assay protocol.

The improved design produces a carrier with improved geometric tolerances relative to commercially available 96 well plates. By "geometric tolerances" is meant the relative differences in well center to well center measurements, well wall profiles, radius of the well base, overall flatness of the carrier, and overall twist in the carrier. Again this makes automated positioning of test surfaces in the carrier easier as well as image analysis of the reacted test surface. All geometric tolerances are set at ±0.5°.

The mold design for the improved carrier includes features that will cause the outer surface of the carrier to appear matte or finely textured. It also contains pattern recognition targets, e.g., at the upper right and lower left corner of every well or indentation, that will appear as a recognizable feature (smooth and glossy circles in the exemplary embodiment). These features provide the automated test surface positioning equipment with orientation and positioning marks so that machine vision can be used to assess alignment as the test surface is delivered to the well. They may also be used in the final image analysis process to improve well alignment, identification, location, and/or spacing, prior to imaging if required. In addition each well of the carrier contains 8 alignment ribs, two on each side of the well, designed to assist in the support of the test surface in the well. These ribs can control the azimuthal ("twist" or "skew") placement of the test surface within the well. The ribs will abut the edge of the test surface when it is positioned in the well. See FIG. 2E. Inside the alignment ribs is an extended window frame feature extending from the well wall that will also support the test surface and assists in maintaining the flatness of the test surface within the well. This feature can improve the ability to automate glue dispensing, as it provides a pocket for the glue dispense, and machine vision systems can be used to control the amount of glue dispensed relative to this extended window. Once placed the test surface is tightly sealed in the well and this serves to minimize the volume of reagents, washes, etc that are trapped under the test surface during analysis. This feature can also serve to minimize contamination in subsequent assay steps.

Image Analysis Instrument Design and Production

An acceptable starting point for the optical component design is the Scanalytics' Elispot instrument. However a more robust support structure and instrument housing are required for routine high volume use. The image analysis instrument includes a CCD camera with at least a 0.5" detector surface and no larger than 10 µm×10 µm pixels, and an array of at least 640×480 pixels. A preferred minimum scan area is 6.3 mm×4.8 mm. The camera should provide digital temperature compensation and have a digital offset control of at least 8 bits, but 12 bits or more is preferred. A minimum full well capacity of 25,000 electrons is preferred. A dynamic range of at least 8 bits, and preferably 12 bits, and a scan rate of 16 MHz is preferred. Readout noise should be no greater than 16 electrons. The spectral range should be 280 to 1000 nm. Anti-blooming factor of greater than 1000 is also preferred.

The camera should mount on an extension tube or other positioning optical hardware to provide the appropriate focal distance and depth. Any desired magnification optics should be included in this portion of the optical path.

A black and white camera is preferred for the thin film applications but a color camera is acceptable.

In one embodiment the optical path including focus, distance to image, and magnification are pre-set and no adjustment is required. In another embodiment for applications, where there may be value in focussing in on a sub-section of an array, an adjustable zoom and focus may be required. Adjustable zoom and focus requires additional motor control and software. One such auto-zoom, auto-focus extension tube set-up is available from Thales Optem.

A diffuse light source is preferred when the signal generation method is a thin film change to provide broad surface coverage of uniform intensity. When a specularly reflective surface is used the diffuse light source will also minimize artifacts in reflection from the specular surface. The intensity and wavelength requirements for the light source will depend on the test surface and thin film signal generation method used. The light source should provide constant and uniform illumination. A thin film generation method can use a white light source that is randomly or linearly polarized. Linear polarized light may also be used to reduce the artifacts from specular reflection. The light source may be filtered to provide a monochromatic incident light. A fiber optic cable can be used to direct light from a light source to the input port in the optical path. A coaxial diffuser module is one option for providing input light to the optical system.

A support system should be provided that includes a base of sufficient stiffness and weight to minimize vibration of the stage as it moves to various positions. A 0.5" thick aluminum plate is adequate for this purpose. The size of the plate is dependent on the stage and optical component dimensions but a 15"×18" plate is generally sufficient. To minimize stray surface reflections the aluminum should anodized or painted a flat black.

The support plate will contain bore holes at various positions. Some of these will be used to attach the support pegs for the x, y stage and some to attach the support structures used to attach the camera and optical components. For a Ludl Biopiont x, y stage 4 support pegs are anchored to the support plate. The stage is then set onto these pegs with socket head cap screws of appropriate dimensions. The height of the support pegs is selected so that the motors and control cables are clear of the support plate and free of any binding but so the height of the pegs is as low as possible to maintain maximum stability. The diameter of the support pegs are preferably designed to match the machined positions in the stage, and are large enough to provide stable attachment of the stage to the support plate.

FIG. 3 illustrates the assembly of an image analysis station. First, remove the lens cap from the Zoom 70XL module (Optem Part #399510-309). Then loosen the upper set screw in the Lower Module Coupler (Optem Part #33-03-63) with the provided alien wrench. Set the Zoom 70XL module into the Lower Module Coupler until is is flush with the Lower Module Coupler outer surface and tighten the set screw. Remove the lower lens cap from the 0.5× TV Tube (Optem Part #29-90-70) and thread onto the upper section of the Zoom 70XL module. Loosen the set screws in the bottom of the Lower Module Coupler with the provided alien wrench and set flush onto the co-axial illumination housing (Optem Part #30-14-00) with the light feed tube to the rear (all Optem labeling should be facing the front of the other components). Tighten the set screws. Thread the polarizer unit (Optem Part # 29-69-02) onto the co-axial illumination housing. Thread the fiber optic housing (Optem Part # 30-16-02) onto the polarizer. Loosen the screw on the fiber optic housing and insert the 10 mm fiber optic adapter (Optem Part # 30-16-01). Tighten the screw. The optical module is ready to install.

When an autozoom and autofocus capability is desired the assembly is modified as follows. Thread the 0.5× TV Tube (Optem Part # 29-90-70) onto the auto zoom/auto focus unit (Optem Part # 39-28-30). Loosen the screw on the attached co-axial illumination housing that is part of the auto zoom/auto focus module and insert the 10 mm fiber optic adapter (Optem Part # 30-16-01). Tighten the screw. The unit is ready to install.

Place the support frame on a bench top and slide the base to the edge of the bench such that the bottom bore holes are visible underneath the base. Apply two rubber support feet and press the adhesive on firmly then attach with two 1032 by ½ socket head cap screws. Rotate the base and repeat this step with the back edge of the base plate. See FIG. 4. Attach the left (FIGS. 5A-5D) and right (FIGS. 6A-6D) support brackets to the Back Support piece (FIGS. 7A-7C) with 3 socket head cap screws on each side then secure the assembly to the positions indicated in FIG. 4. Attach the Camera Support Plate (FIGS. 8A-8B) to the top of the left and right support brackets with 4 socket head cap screws.

Figure 7B:
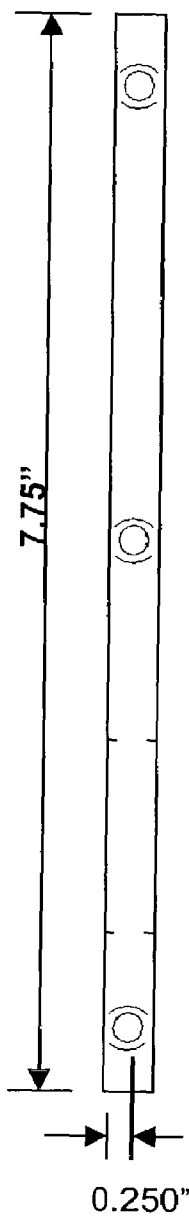
FIGS. 7A-7C illustrate an embodiment of a back support for the image analysis instrument.
Figure 7A:
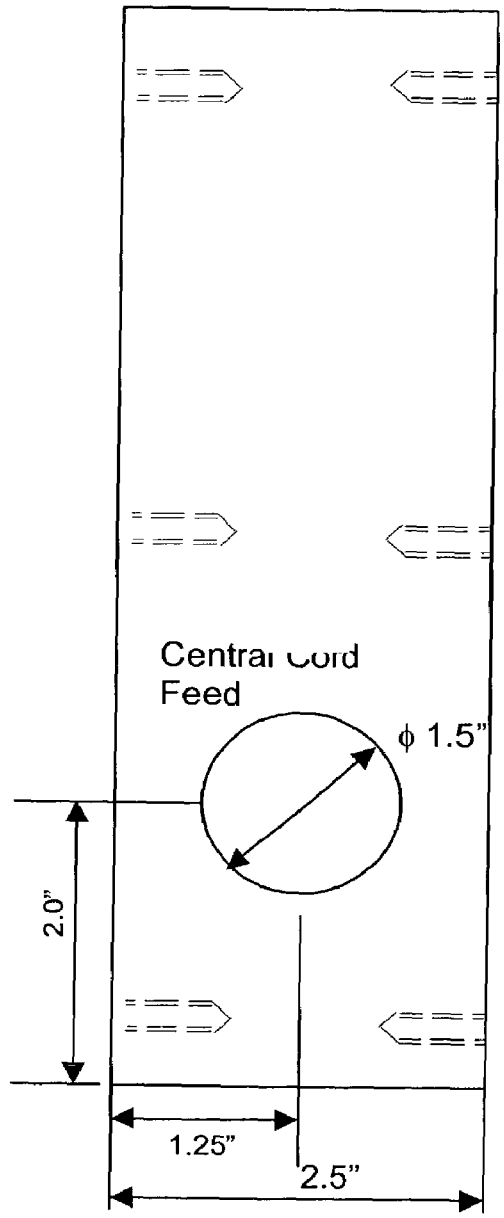
Figure 7C:
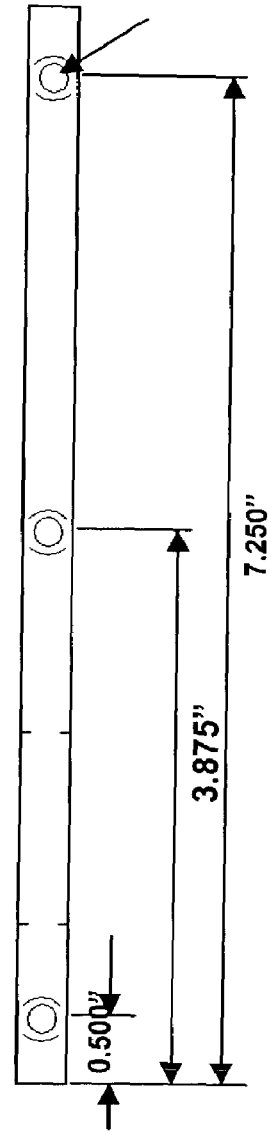

Mount the motorized stage component onto the four stage support pegs with four 1032 by ½ " socket head cap screws so that the motors on the stage are at the rear of the support structure. Attach the x- and y-stage control cables to the labeled motor and slide the clamping mechanism into place. An acceptable stage is the Ludl Electronics BioPoint or Bio-Precision stages depending on the need for feedback control. Feed the other end of the control cables through the center hole of the back support plate (FIGS. 7A-7C). Place the control box and the joystick for the stage control to the side of the support frame. Attach the power cable to the control box and then plug into a surge protected power outlet or to a power conditioning unit. Attach the joystick control cable to the control box and the computer serial port cable to the proper slot on the control box.

Thread one micrometer into each of the three linear stages using the supplied wrench. Place one of the completed linear stages onto the Camera Support Plate so that the micrometer is on the right side of the platform when viewed from the front, and the open slide structure is to the upper surface of the assembly (FIGS. 8A-8B). Fasten the linear stage to the support plate with four 440 by ½" socket head cap screws. This allows for the y-axis camera translation. Linear stages may be purchased from Thermo Oriel or Newport.

Place a second completed linear stage at 900 to the first linear stage and fasten with four 440 by ½ " socket head cap screws. The micrometer is positioned to the rear of the instrument and the open slide structure is the upper surface of this assembly. This allows for the x-axis translation of the camera. Fasten the angle bracket (Newport) onto the second linear stage with four 440 by ½" socket head cap screws so that one face of the bracket is to the front of the instrument and the other covers the linear stage.

Attach a third completed linear stage to the front face of the angle bracket with the micrometer pointing down and the open slide structure faces out from the angle bracket. This allows for the z-axis translation of the camera.

Figure 10A:
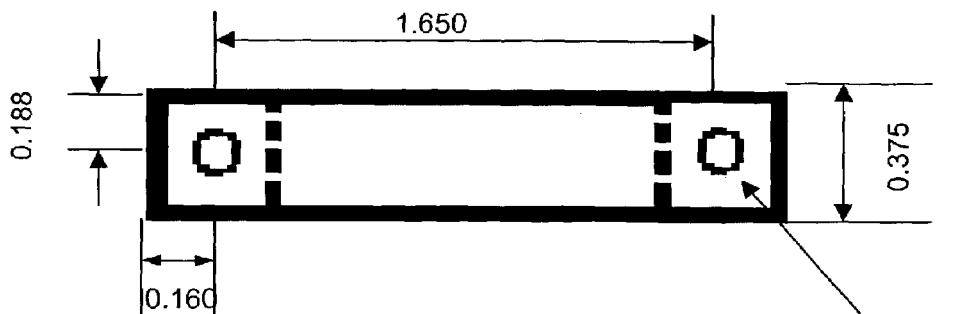
FIGS. 10A-10B illustrate an embodiment of an extension tube clamp for the image analysis instrument.
Figure 10B:
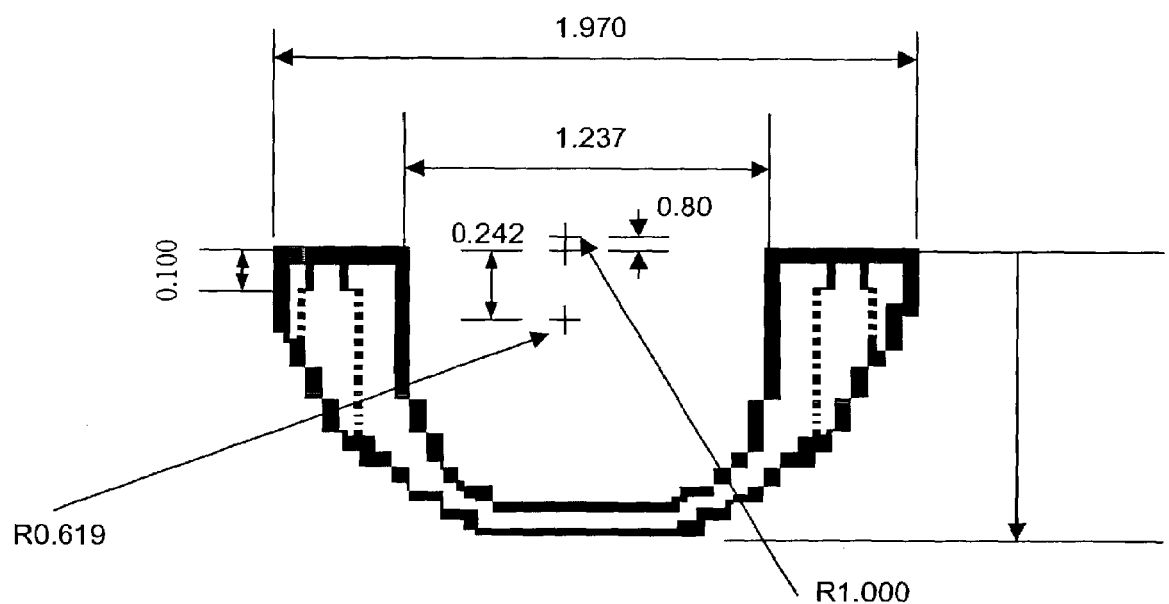

Attach the extension tube support block, see FIGS. 9A-9C, to this linear stage with four 632 by ⅜" socket head cap screws. Place the completed optical assembly so that the extension tube is centered in the well of the support block and the upper portion of the 70XL zoom module is at the bottom (abutting the bottom) of the support block and hold it place. Use 2 semi-circular clamps, see FIGS. 10A-10B, to attach the extension tube to the support block with two 632 by ⅜" socket head cap screws for each clamp. Be sure that the optical assembly is straight in the housing and firmly attached.

Attach the CCD camera to the upper end of the extension tube of the optical assembly by threading on the camera. The camera should be square with the surface of the camera mount plate facing the front of the system. Attach the camera control cord by plugging into the top of the camera and thread the cable through the center hole in the back support plate.

Insert one end of the fiber optic bundle into the fiber optic adaptor of the optical assembly and tighten the set-screw to secure the fiber optic cable. Run the fiber optic bundle through the center hole in the back support plate.

Figure 4:
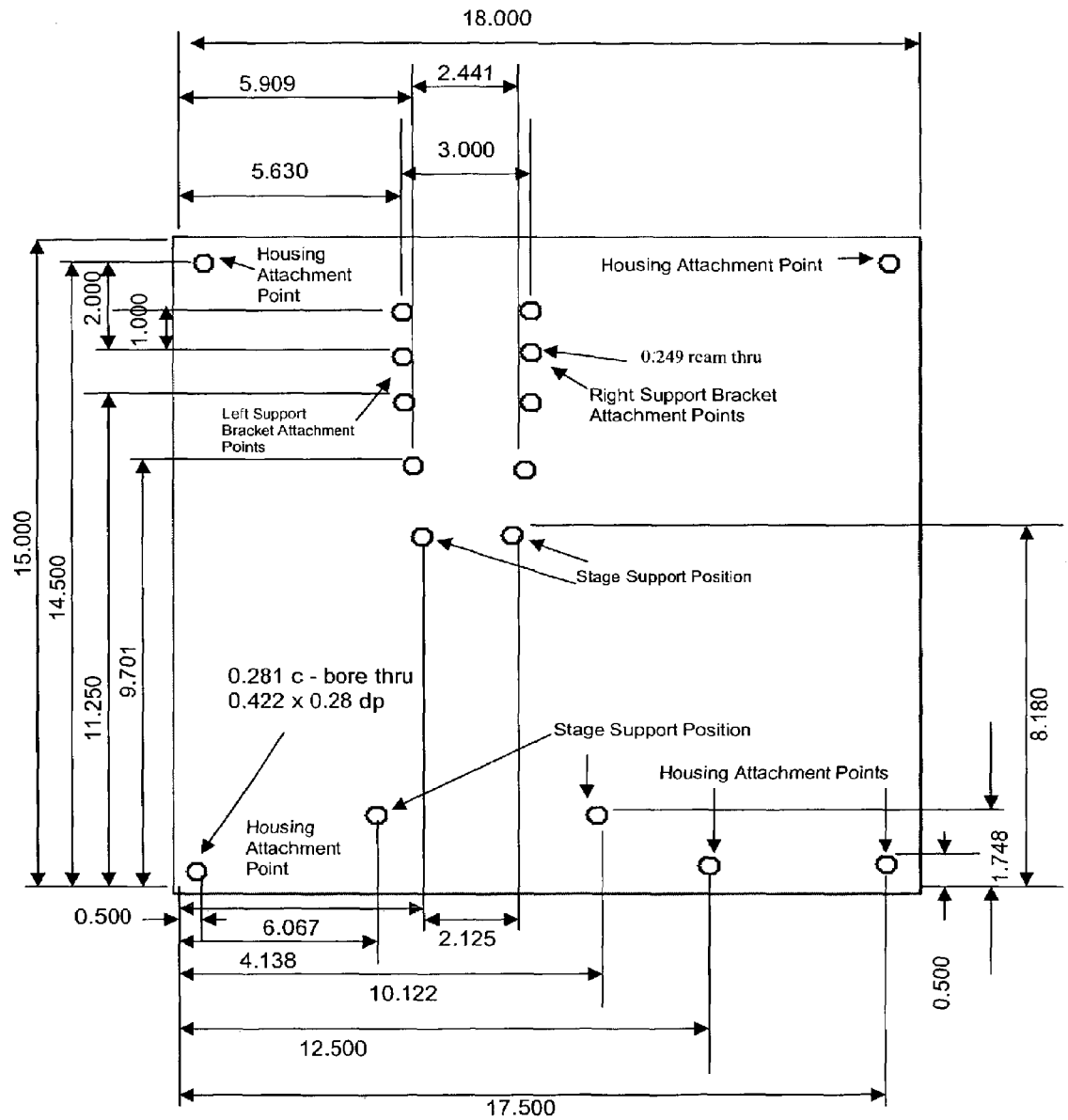
FIG. 4 illustrates an embodiment of a base support plate for the image analysis instrument.

Place the light source next to the stage controller on the bench and attach its power cord and plug into a surge protection power outlet or a power conditioning unit. Feed the other end of the fiber optic cable into the light source outlet port and tighten the set screw. Carefully slide the housing assembly over the optical components and stage feeding all the cables through the insets in the housing. The fiber optic and camera cable feed through the center support structure and the stage cables feed through the side insets. The housing assembly is made by cutting 0.5 cm thick polycarbonate sheets to the appropriate dimensions. The polycarbonate sections are joined with aluminum railing and rubber gaskets into a square cover that fits into the Base Support Plate as shown in FIG. 4. The polycarbonate is bronze colored or smoked colored to assist in the removal of interference from ambient room light if the detection system is sensitive to background lighting. Sealing the left side and lower left front panels of polycarbonate into aluminum support rails that are hinged creates two access panels. The side panel provides access to the complete system for any maintenance or cleaning required. The front panel provides access for placement of the test surface carrier into the stage-positioning insert. Each hinged panel includes an attached handle and a magnetic locking feature to seal the doors. The polycarbonate housing also protects the stage and optical path from dust and other contamination between and during measurements. The housing is 23.75" in height to allow clearance above the camera and its cable which are the tallest feature of the instrument. The rear section of polycarbonate contains cut-outs for the exit of all cables from the various components to the computer or appropriate controllers.

Carefully slide the covered system to the front of the bench exposing a small portion of the bottom of the support base and attach the cover to the base with three 1032 by ½" socket head cap screws. Three screws are required in the front panel because of the access door. Rotate the instrument and repeat this attachment protocol for the backside using two screws. Rotate the instrument to the proper orientation and place in the center of the bench so the instrument is well removed from the edge.

Place the computer monitor, keyboard, mouse, and computer tower beside the light source and the stage controller. Attach the power cord to the monitor and plug into a surge protected power outlet. Attach the computer connection to the monitor. Open the computer tower case according to manufacturer's instructions and install the image acquisition board and any stage control boards required. Reseal the case. Attach the power cord to the computer tower and plug into a surge protected power outlet or power conditioning unit. Attach the stage control cable to the board interface. Attach the camera cable to the serial port plug in. Attach the monitor cable, the mouse cable, and the keyboard cable to the computer tower per manufacturer's instructions.

Test surfaces to be analyzed by this system could be configured similar to microscope slides and the x, y stage will contain an insert that secures the slide for reproducible positioning within the stage. The test surfaces can be the mounted in the bottom of a welled plate of any well size and again an insert is used to secure the plate reproducibly within the stage.

Software Design

The goal of a software package for image analysis of biological or chemical arrays would be to be completely free of user intervention. All steps beyond initial set-up and calibration should occur automatically. Appropriate setup and calibration steps include setting an initial light intensity from the light source and manually verifying test surface alignment with the stage positioning controls would be included. It is preferable that all steps be under the control of the software.

The disclosed embodiments may be implemented in a variety of ways. For example, the disclosed methods can be implemented as either software or firmware. Further embodiments may be hardware implementations including, for example, field programmable gate arrays (FPGAs).

To date the primary limitation in meeting this goal has been identifying the location of the array on a test surface and correcting for skew of the array in the image, dealing with spot size and shape variations, reflections, "wavy" rows and columns of spots, and then correctly assessing the number and location of the elements within the array. Also addressing variations in the spot morphology, or arrays that have low spot redundancy or few elements in each row and column of the array have prevented complete automation of the process. Qualitative and quantitative treatment of the data collected is possible.

For the initial discussion, it will be assumed that a positive array element will be visualized as a dark feature on a light background. However, the algorithms can easily be adapted to detect a white element on a dark background or a specific color against another color-essentially any situation that produces sufficient contrast between the positive array element and its background.

The embodiments of the image analysis algorithm provide an Application Programming Interface (API) allowing the algorithms to be run through a special purpose user interface, such as is done for testing purposes, and as an extension to a more general purpose software package, such as an image capture and reporting program. Further, this modularization of the algorithm behind an API enhances portability across operating systems. For example, the algorithm can be packaged as a Dynamic Link Library (DLL) on Microsoft Windows, or as a Shared Library on Linux. In addition, the API makes the algorithms more independent of programming languages used in other parts of a system. For example, the algorithms have been implemented in C, but can be used by other programs written in C++, Delphi, Visual Basic, and Java.

Skew in the array can be generated at a number of steps in the production of the test surface. The spotting technology used to apply the individual capture reagents can introduce systematic misplacement of the spots that result in a skewed array. The separation process used to generate individual test surfaces can introduce skew by being out of square or creating non-uniform edges. The positioning equipment can place the test surfaces in the carrier slightly out of square. Any intrinsic bow in the test surface bulk material can generate skew of the final positioned array as can any bow in the test carrier itself. An edge may be a physical edge as for an individual test surface or may be a physical barrier or marking used to segegrate individual arrays that provide contrast relative to the rest of the image or test surface.

A proper spot finding algorithm is the first step in achieving the desired result. This protocol will not only address any twist in the imaged array but will address the flatness of the imaged array, general poor quality of the array, non-specific binding in the array, and illumination defects. One such algorithm in the first step "squares" the image of the test surface. This reduces any side-to-side or up-and-down drift in the columns and rows of spots in the image not due to misplacement of individual elements of the array.

Squaring the test surface involves forming two vectors of pixel sums. One vector represents the sums of all columns of pixels in the image. The other is the sum of all rows of pixels in the image. For each of these vectors of sums, the squared first derivative of the vector is generated. With the image size used in the NucleoSight imaging station, this is accomplished by using a Savitsky-Golay filter with a kernal size of 20 or a value that is appropriate to the image and signal being analyzed. Two strong peaks in each of the squared derivatives represent the edges. The quality of the edges can be estimated from the height of the peaks in the squared derivatives. A multiple of the standard deviation for the squared derivative can be used as a quality criterion for the edges. If the peaks in the squared derivative do not rise some multiple of the standard deviation above the mean, an edge can be disqualified as too poor to continue the squaring operation.

If satisfactory edges are detected, a simple search is done for a rotation of the image that generates the strongest peaks in the squared first derivative. Essentially, a 0.25-degree rotation is attempted and the above summing and derivatizing steps are repeated. If the size of the peaks in the squared derivative decrease, the direction of the rotation is reversed. Otherwise additional rotations are done and the resulting peak strength examined. The process is repeated until the peak strengths pass their maxima. At that point, the original image is rotated one step back from the rotation where the decreased peak strength was observed: This "backing up" returns the image to the rotation that produced the best peak strengths. This corresponds to the rotation with the sides of the test surface most vertical and horizontal. If at any time during the rotation search the results from all four sides do not agree, a "voting" algorithm is used to determine whether the search should proceed. In that case, three of the four sides must experience an improvement (higher peak height) for the search to proceed.

After squaring the image of the test surface, an attempt is made to locate the grid of spots within the image. Because the spots are arranged in relatively regular rows and columns, the sums of column and rows of pixels tend to show distinct peaks at the positions of columns and rows of spot. The peaks in these pixel sums can be used to locate the spot grid as a whole. For this process to work, all four edges of the test surface must be detected in the image, otherwise, processing stops. In practice the sums are first "inverted" by subtracting the sum for each pixel column or row from the largest sum for the pixel columns or rows. This transforms the data into a form in which positive-going peaks in the sums represent the presence of a column or row of spots. The second derivatives of the inverted pixel sums are then generated—one for the horizontal pixel sums and one for the vertical sums. A Savitsky-Golay smoothing/derivatizing polynomial is used to generate the derivatives. The size of the smoothing kernal is set larger than would usually be the case in order to supress unimportant detail. This leaves the positions of the spot rows and columns intact but smoothes away width information.

A region of the second derivative is searched for minima between the edges of the test surface. Starting and stopping the search at an "inset" from the test surface edges further reduces the search area. An inset of about 3% of the test surface width or height seems to work well. This inset moves the search away from the large changes in the second derivative at the test surface edges. The minima in the second derivatives represent peaks in the sums. For a minimum to be considered valid, its absolute value must exceed some predetermined "cutoff" value. If a peak meets this cutoff, its position is recorded for later use.

The peak search of the second derivatives is handled slightly differently when searching for columns or rows of spots when the occupancy of the column is minimal with respect to other columns or rows in the array. The algorithm detects the high occupancy columns or rows and interpolates the positions of the undetected columns. The algorithm confirms the validity of the interpolated column or row by examining the spacing between detected columns or rows. Spacing should be nearly regular. If an extraneous row or column is detected, the spacings are not so regular. If insufficient numbers of strong peaks are detected, as for an empty well or an unreacted test surface, the algorithm stops further analysis and returns a code indicating the reason analysis was stopped. This code is returned in the table of results in order that the user may see the reason for the failure.

When all needed spot columns and rows have been detected and interpolated, the algorithm moves the starting position of the grid that is used later in the algorithm to refine the positions of individual spots. Next, any needed preprocessing of the image is done. For example, smoothing, dilation, etc. The current version of the algorithm does a median filtering operation with a kernal size of 3.0. The size of kernal selected will depend on the image and signal being analyzed.

The next step is to apply an adaptive thresholding operation to the processed image. This binarizes the image for subsequent analysis steps. An adaptive threshold is used since no single threshold value exists which can reliably binarize the image due to variations in background on the test surface, variations in illumination due to test surface tilt, etc. Both a mean adaptive threshold and a median adaptive threshold have been used. No advantage of one method over the other was observed.

A morphological closure (erosion followed by a dilation) is applied at this point. This procedure closes small "holes" in the thresholded image that might interfere with the subsequent spot-searching algorithm. The sizes of the kernals used in the closure are small, 2 pixels for the erosion, 3 for the dilation. A larger kernal for the erosion was found to connect regions of background. The larger kernal for dilation helps break up connected background areas somewhat. For a quantitative analysis, this step may not be advisable.

After a thresholded version of the image is obtained, it is examined for spots of the appropriate size and shape. A default grid is used to estimate where reacted spots should appear. The program starts its search within each grid cell by examining the very center pixel in the cell. If the pixel is black, the program looks for the center by searching in the horizontal and vertical directions for the next white pixel. If the search indicates that the starting point was not centered, either horizontally or vertically, the starting point is moved to the center and the search step repeated. For most real spots, only a few search steps are needed to determine the center. In any case the number of center search steps is limited to 5 steps for the analysis of thin film images.

In the event that the initial pixel examined in the center of the cell is not black, the algorithm divides the cell into four quadrants, estimates the average intensity of each quadrant and tries to start the search again in the center of the darkest quadrant. If the center pixel of the darkest quadrant is also white, the search stops. Otherwise the search for the center of the spot proceeds as described in the previous paragraph. If the width and height of the detected spots are within a prescribed range, and the ratio of width to height is also in a prescribed range, the grid cell is moved to the new location.

After all cells in the grid have been searched, they are examined to determine if any adjacent cells moved to the same location. This type of "collision" can occur if the initial grid location nearly bisects the location of actual spots on the test surface. Any cells that have collided are returned to their original locations.

After reversing collisions, the reliably detected spots, those with acceptable size and shape, are examined for a systematic horizontal and vertical offset from the starting position. The program determines a horizontal offset by averaging the difference in horizontal positions of all reliably detected spots in columns 1, 3, 5, and 7 from their starting positions. Similarly, the program determines a vertical offset by examining reliably detected spots in the first and last rows of the grid. These rows and columns are used for one specific set of analytes and may be changed for different analyte layouts on the test surface. When the vertical and horizontal offsets have been determined, the location of the original grid is adjusted by these offsets, re-applied to the thresholded image and the spot search repeated. Although collisions have never been observed after this step, the algorithm still looks for them and will reverse them if detected.

Although the second search step rarely detects additional strong spots, it provides a much better estimated location for weak or un-reacted spots. Without the adjustment, background signal estimation is not good for unreacted spots and weak spots might be missed altogether.

After the spot searching algorithm has finished, the "signal" for each cell is determined by subtracting the average intensity of a circular region in the center of each cell (22 pixels in diameter) from the average intensity of pixels arranged in a "frame" around the center. At the moment, this frame is 35 pixels on a side and a two pixel thick frame is used or about 270 pixels contributing to the average. It is not believed to be significant that a rectangular frame is used; it is just computationally convenient. The pixel selection is based on individual element size (spot size) and image acquisition parameters like the fold magnification, etc.

To obtain a signal for each cell, the average intensity of the dark center region is subtracted from the average intensity of the lighter surrounding frame. Since lighter pixels are represented with higher intensity values, performing the calculation in this way produces more positive signals for "stronger" spots. When all signal processing for a test surface has been completed, the locations used for signal calculations are marked on the image in the form of a small "+" sign at the center of each spot. Although this happens too fast for the user to see during the actual plate run, the image of each well is recorded with these markers for later reference, if needed.

The program locates the spot grid even if the test surface image is misaligned due to spotting, breaking, test carrier placement, stage movement, or user alignment problems. If a test surface has reacted spots and all sides of the test surface are visible and clean in the image, the algorithm should correctly locate the spots. Empty wells and wells in which the test surface is not developed are usually detected earlier in the analysis process. Once detected, no additional analysis is done on those wells. If the algorithm determines that a particular well should not be analyzed, it returns a code that can inform the user of the reason the analysis failed.

When the algorithm generates the data table for a particular well, the table includes the position of each spot in the image as well as the background, foreground, and net signals. Although this information need not be used in the fully automated plate run, it can be used to analyze individual test surfaces manually. The algorithm adds a small marker, a "+" symbol, at the location of each spot center. The images with the markers are saved during the fully automated plate runs. If there is ever any question about whether a spot was detected successfully, the image can be retrieved and checked for the location of the marker.

Where of value the area of the array element can be calculated from the number of pixels giving above a thresholded value or some other calculation. Individual pixel responses for the identified element can also be recorded or a histogram of the pixel intensities can be generated. Other displays of the data are possible and known in the art.

A preferred approach to the spot finding algorithm is to remove the requirement to place a grid (corresponding to the number of elements in the array) over the image with an approach that simply identifies and confirms the placement of the individual elements in the array. To identify the individual elements in an array the algorithm must first determine that the element is roughly of the size, shape, and position expected for the size of array being analyzed. For this purpose, a Hough Transform is applied. The algorithm specifically searches for geometric primitives such as lines or circles depending on the exact transform used. It can also be made to look for a maximum in the transform space that would correspond to the location of an object in the real space or an image. These transforms have been used for the detection of craters in images of various planets and for digitizing engineering drawings. The crater detection technique is of value because it works with uneven illumination or an uneven background. It also works when the circles are not in a rigid arrangement, and for circles that are both brighter and darker than their surroundings and where the circle diameter is not a constant.

The steps in this protocol create a list of the locations of reacted spots for any image. Then based on pre-set selection rules decides which of these spot locations are noise and eliminates the noise. Any spot determined to be an actual spot location is assigned to a specific element in the array based on a pre-determined array map. Unreacted spots are assigned a location in the array based on the spacing of the identified elements in the array. From the intensity data for each assigned location the presence or absence or absolute value of each element in the array can be established.

Figure 11A:
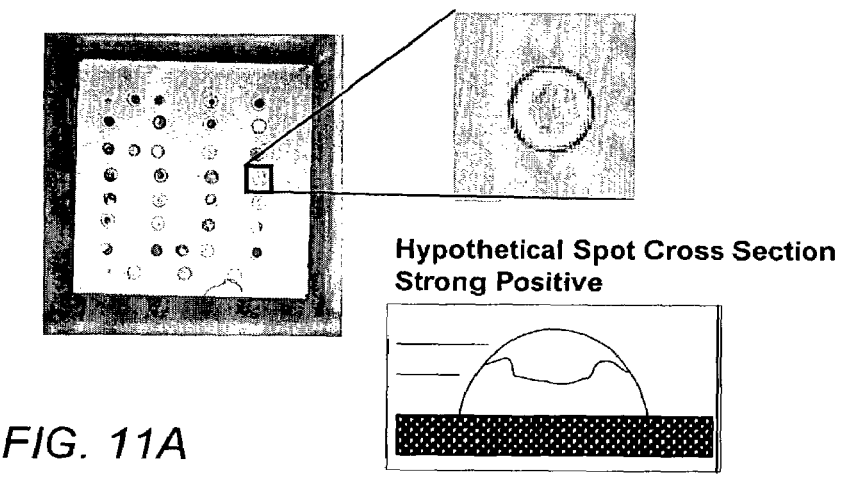
FIGS. 11A-11C illustrate exemplary formation of spots in an arrangement according to the invention.
Figure 11B:
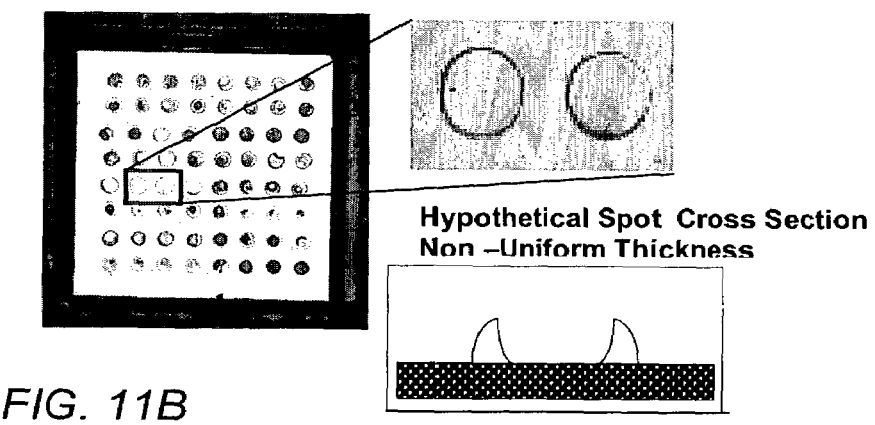
Figure 11C:
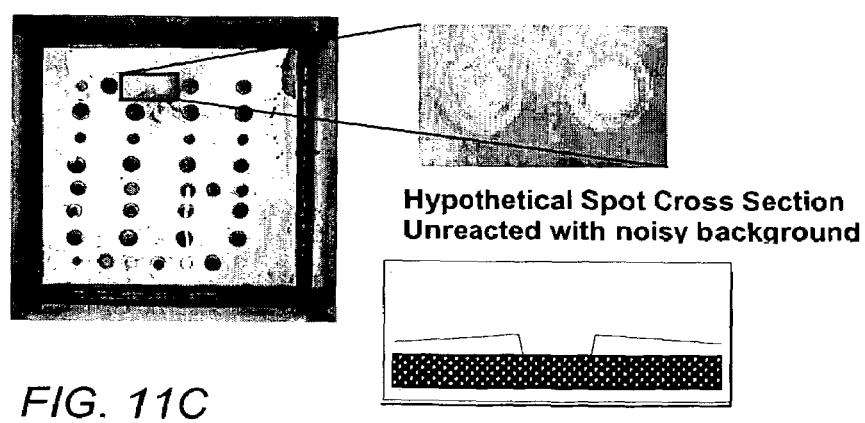

A unique feature of the thin film detection assays is that for very strong reactions where the film thickness or bound mass has caused the color change to move into a second color fringe, the reaction produces a spot that is brighter than the background in a grayscale measurement. Thus a positive spot may be darker than the background or lighter than the background and still be a valid positive result. In addition the spots formed may not be of uniform thickness. See FIGS. 11A-11C. For this type of test surface, and for other methods of signal generation, it is important that the algorithm selected correctly detect and assign a positive signal to dark spots, strong reaction spots, and the non-uniform spots without calling an unreacted spot even in the presence of a noisy background. If background is generated in the assay protocol then unreacted spots can appear as bright spots in a dark background, see FIG. 11C. The image processing method must adequately account for this type of processing issue.

In this case the Hough transform approach alone is limiting because the processing time is too long. It was recognized that the images produced in this type of thin film assay but in other applications as well have a strong signal gradient moving from light to dark in the center of the spot. The unreacted spots also have a strong gradient but it moves from dark to light toward the center of the spot. See FIGS. 12A-12B.

For these surfaces the processing alogrithm with the best performance consists of the following processes, as illustrated in the method 100 of FIG. 1. First it locates the test surface image, although this is an optional process. Then, the image is cropped to remove the dark edge in the image from the plate well. Again this is an optional step but reduces the amount of data to be examined to allow the algorithm to operate more quickly. It also has the advantage that any noise around the edge of the image is not detected or examined. To accomplish the cropping, projections of the image are made in both the horizontal and vertical directions. First derivatives of the two projections are generated using a Savitsky-Golay smoothing/derivatizing polynomial of order 3 and a kernal size of 21 elements. Other values may be selected based on the particular application, device format, and signal generation method. Then the derivatives are squared and scanned from the edges toward the center for the first peaks rising 4 standard deviations above the mean value of the squared derivative. The centers of the two peaks so detected from each squared derivative are considered to be the locations of the edges of the test surface along the relevant axis. After the test surface edges have been detected (block 102), the image is cropped (block 104) to those edge locations, typically representing a reduction in image size of about 25% fewer pixels. If the test surface edges are not detected, the step in block 104 is bypassed, and processing continues without a reduction in the image size.

The value of 4 standard deviations above the mean used for detecting peaks in the squared derivatives was arrived at empirically. The value chosen was set to eliminate false detection of reflections as actual test surface edges. Lower values cause reflections to be incorrectly called test surface edges. Setting the cutoff as high as it is places constraints on the quality of the actual test surface edges and the rotation of the test surface in the image. If the test surface edges are chipped, uneven, or obscured by non-specific binding, the cropping operation may fail. Likewise, if the test surface is rotated beyond about four or five degrees, the cropping operation may fail. The degree of acceptable rotation varies with other qualities of the test surface image, such as overall brightness, "cleanliness" of background on the test surface, etc.

As mentioned above, failure to crop the image is not fatal to the spot finding algorithm. It just results in a slightly longer analysis and may require dealing with more spurious noise spots.

At block 106, gradients of the image are generated in both the horizontal and vertical directions. The gradients are generated by convolving the image with the 5 by 5 sets of coefficients proposed by Ando (Shigeru Ando, "Consistent Gradient Operators", *IEEE Transactions on Pattern Analysis and Machine Intelligence,* 22(3):252-265, 2000.) Taking the arctangent of the vertical gradient divided by the horizontal gradient generates the directions of the gradients (block 108). In the event that gradient in either direction is less than the absolute value of the minimum representable single precision floating point number on the system, the direction is set to 0. Note that the order of generating the gradient directions and the squared gradient magnitude and thresholding, described next, is not believed to be significant. At block 110, squaring the gradients in the horizontal and vertical directions then summing the results generates the squared magnitude of the image gradients. A more traditional approach would be to generate the image gradient magnitude by taking the square root of the sum. Eliminating the square root step provides a speed bonus and does not expose the algorithm to the possible numerical domain problems that might occur with the square root operation. The squared gradient magnitude may be binarized by a thresholding operation (block 112). All pixels with a squared gradient magnitude greater than the mean of the squared gradient magnitude are set to 1 in the thresholded version of the image. All pixels with a lower squared gradient magnitude are set to 0.

The use of a multiple of the mean of the squared gradient magnitude to threshold the image was arrived at empirically. Examination of sample images indicated that a multiple of the mean worked well. The value of 1 times the mean appeared to work well for thin film images. It is possible that some other measurement of the square gradient magnitude could be used, such as some multiple of the variance or median. The overall quality of typical images might also influence the selection of the cutoff. This step is not absolutely required for the remainder of the algorithm to work. However, it focuses the remainder of the work on the pixels of interest. This usually eliminates about 90% of the image pixels from further examination, greatly speeding the analysis.

In the next step of the algorithm, at block 114, information from the gradient directions, gradient magnitude, and acceptable spot radius is combined to generate a transform of the original image that discloses the positions of acceptable spots.

At the edge of a circle, the gradient "points" along a line perpendicular to the tangent. The gradient can point toward the center of the circle or away from it, depending upon whether the circle is dark on a light background or light on a dark background. For a perfectly defined circle, all of the lines pointing along the gradients toward the center of the circle will intersect at the center of the circle. As the circle deviates from an ideal shape, the intersections may become fuzzy, but will still tend to locate the center of the circle.

The sense of the gradient is defined to point toward the center of circles when it makes the transition from a light background to a dark circle. This causes the gradient to point toward the circle center for dark circles on light backgrounds, for white circles, which, because of the physics of the test surface, have a dark ring surrounding the white centers, and for "donuts" where the indicator may have flaked away, leaving a dark ring on a light background. In the event that an unreacted spot is surrounded by dark, non-specific binding material, the light spot surrounded by a dark background causes the gradient to point away from the circle center, as desired. For this step of the algorithm, a new, empty (all 0) image is created. For every non-zero pixel in the thresholded squared gradient magnitude, the gradient direction is retrieved. The gradient direction is used to build a line segment pointing toward the center of a possible circle. The acceptable circle radius determines the end points of the segment. Every pixel in the newly created image corresponding to a pixel in the line segment receives a "vote". That is, every such pixel has its intensity incremented by one. As successive pixels in the thresholded squared magnitude are examined and line segments generated, the pixels in the new image corresponding to the centers of circles of the appropriate size tend to accumulate more votes. At the end of the process, the gradient magnitudes and directions have been transformed into a representation of the original image where circle centers have higher intensity values than the background. See FIG. 13. While this approach was designed to address the optical thin film test surfaces, the algorithm can address any detection format where these types of image variations can negatively impact the interpretation of the image.

The current implementation of this step makes no optimizations in terms of "splitting" votes between adjacent pixels when the line segment does not fall exactly through the center of the pixel. Neither does it contain optimizations on the generation of the line segment such as a Bresenham line generator. Such improvements might be made if needed, but that has not been the case so far.

Just as with the squared gradient magnitude, applying a thresholding operation generates a binarized version of the transform (block 116 of FIG. 1). In this case, the thresholding criterion is to use some fraction of the maximum vote count from the transform. Empirical investigation indicates that a threshold of one seventh the maximum vote count works well for thin film images. So, in the thresholded transform, pixels corresponding to pixels from the transform with a vote count greater than one seventh the maximum vote count are set to one. All others are set to 0. It is possible to imagine other thresholding criteria that might work. The use of a fraction of the maximum vote count causes many spurious spots to be detected in images of empty wells. Since no pixels receive very many votes, many pixels, often over one thousand, receive enough votes to exceed the threshold. Later stages of the algorithm declare these images and spurious spots to be uninterpretable and they are eliminated.

Usually, spots in the thresholded transform are represented by contiguous groups of pixels. At this stage in the algorithm, at block 118, those contiguous pixels are detected. All pixels in the same contiguous region are assigned a label. A small positive integer is used to represent the spot number. For each contiguous region of pixels in the thresholded image, only one pixel may be used to represent the location of the spot (block 120). Combining the information from the transform and the labeled regions, the pixel in the region corresponding to the pixel in the transform with the most votes is set to one. All other pixels in the region are set to 0. It some times happens that a spot, or a spot and noise, are represented in the thresholded transform by two or more non-contiguous regions. In the next step of the algorithm, pixels from the first stage of suppression are examined for near neighbors. "Nearness" is defined using the same spot size criteria used to generate the transform. If two or more pixels are determined to be within the acceptable spot radius of one another, all but the single pixel with the most votes in the transform are set to 0, thereby eliminating the close neighbor (block 122).

By this step in the algorithm, all acceptable spots have been detected and localized to a single pixel that best represents the location of the spot. Except for the selection by spot size, the algorithm is completely general to this point and applicable to any spot-locating task. Subsequent steps in the algorithm apply knowledge of the array layout to associate each spot with an array element and to determine where measurements should be made on the test surface. These steps build a "grid" to match the array layout.

Candidate rows and columns in the grid are estimated by a clustering algorithm known as the "Leader-Follower" algorithm. The clustering criterion used is based on the same maximum spot size criterion used in the Hough transform. At block 124, certain spots or clusters may be eliminated as noise, and a spot grid may be located. Spurious clusters may be eliminated if they are too close to the edge of the test surface. This step is dependant upon the successful detection of test surface edges during the cropping stage described above. If clusters are detected within some critical distance from the edge, they are eliminated as probably being due to chipping, wash effects, or other debris.

The spots remaining are counted in an effort to determine the type of sample that was applied to the test surface, if any. The spot count is used to partition the sample between a blank, patient sample, high-density sample, or empty well. The spot count ranges for these samples need not be contiguous as there are some counts that are not likely to be produced by any legitimate sample type.

At this stage, a set of heuristic rules is used to validate the remaining spots and clusters. If a cluster does not meet the conditions set down for that particular location, it is eliminated and the next cluster is examined. It is frequently the case that the clustering information does not completely specify the positions of all of the rows and columns in an array. For example, in the array of FIGS. 12A-12B the eighth column often has no spots appear and produces no candidate cluster. In these cases, the algorithm will attempt to interpolate the position of the missing cluster. For example, when only seven legitimate columns are detected, the algorithm will examine the spacing of the detected columns and determine if the missing column is one of the edges or a column internal to the grid. Once the determination is made, an estimated position for the missing column can be made based on spacing information from the detected clusters.

When all of the needed grid rows and columns have been detected or estimated from the cluster information, the list of candidate spots is examined to find the spot closest to each intersection of the grid rows and columns. When a match is found, the grid location is moved to the location of the spot. If no suitable candidate spot is detected, the grid intersection is not moved. The criterion for whether a spot is "close enough" to a grid location is again based on the acceptable spot radius used in the Hough transform step.

Signals for each grid location, whether a spot was detected there or not, are generated by summing the gradient magnitude within the maximum acceptable spot radius (block 126). If a spot was detected near the grid location, as determined in the previous step, the signal is measured at the location of the spot. Otherwise, the signal is measured at the theoretical location of the grid point. An image can be returned to the acquisition software package with the center point of the measurement location marked with a small plus ("+") sign (block 128). These signal values, along with the locations of the center of the measurement, are used to build a table of information passed back to the interface/acquisition software package and recorded as the readings for the test surface.

By applying the spot transform to the complete gradient magnitude and not the thresholded version we can increase the sensitivity of the detector. After detection, the signal can be measured by taking the average of the gradient around the detected spot. Cluster qualification rules may require adjustment. A number of the various cutoffs used throughout the alogrithm may need to be set at less strigent values to improve the sensitivity or differentiation of spot signal. This must be balanced with any increase in spurious spot detection or influence of background on the alogrithm's output. In particular the vote divisor should be modified to a larger number. One approach would be to use the existing alogrithm to find the grid then follow with one or more interative passes using thresholds to yield more sensitive spot detection. The first algorithm would be used to confirm the appropriate spot location and the second would be used to determine the true intensity of the spot at that location.

It will be readily apparent to those skilled in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Arrays designed to detect genomic target DNA sequences related to cystic fibrosis ("CF") from a sample following PCR amplification are described below. The test surface is an optical thin film surface that detects hybridization of target sequences to complementary immobilized capture sequences. The optical signal generated is a function of the change in optical thickness due to the hybridization event. The optical surfaces reflect incident white light such that specific wavelengths are attenuated or eliminated resulting in specific color changes. In the absence of a change in optical thickness, the reflected light maintains the original or background color.

Genomic sequences detected by the CF surfaces are specific to 25 mutations and polymorphisms within the CFTR gene and are shown in the following table:

| FM | 2184del A WT | 2184del A Mut | 5T | 7T | 9T | CC | Neg |
|---|---|---|---|---|---|---|---|
| ΔF508 WT | ΔF508 Mut | I148T WT | I148T Mut | ΔI507 WT | ΔI507 Mut | G542x WT | G542x Mut |
| G551D WT | G551D Mut | W1282x WT | W1282x Mut | N1303k WT | N1303k Mut | R553x WT | R553x Mut |
| 621 + 1G > T WT | 621 + 1G > T Mut | R117H WT | R117H Mut | 1717 − 1G > A WT | 1717 − 1G > A Mut | A455E WT | A455E Mut |
| R560T | R560T | R1162X | R1162X | G85E | G85E | R334W | R334W |

| FM | 2184del A WT | 2184del A Mut | 5T | 7T | 9T | CC | Neg |
|---|---|---|---|---|---|---|---|
| WT | Mut | WT | Mut | WT | Mut | WT | Mut |
| R347P WT | R347P Mut | 711 + 1G > T WT | 711 + 1G > T Mut | 1898 + 1G > A WT | 1898 + 1G > A Mut | 3120 + 1 G > A WT | 3120 + 1 G > A Mut |
| 1078del T WT | 1078del T Mut | 3849 + 10kbC > T WT | 3849 + 10 kbC > T Mut | 2789 + 5G > A WT | 2789 + 5 G > A Mut | 3659del C WT | 3659del C Mut |
| FM | F508C WT | F508C Mut | I506V WT | I506V Mut | I507V WT | I507V Mut | FM |

FM — Fiducial Marker
CC — Chemistry Control
Neg — Negative Control

Each CF optical thin film test surface contains a 64-element array. The array consists of paired mutant and wild type positions for each of these 25 mutations. In addition the CF surfaces contain positions to detect 6 polymorphisms. Nine probe sequences detect these polymorphisms within the 64-element array. In addition to the 59 CF elements, the array contains three fiducial markers (FM) and two process controls.

Reagent Preparation:

| 1X Hyb Buffer | 250 mL | 20X SSC |
|---|---|---|
| | 10 mL | 10% SDS |
| | 5 gms | Casein |
| | to 1 Liter | RNase/DNase Free H$_2$O |
| | pH = | 7.0 ± 0.2 |

An insoluble precipitate will immediately form. Heat to 50° C. until fully dissolved. Filter through a 0.2µ cellulose acetate filtration unit. Aliquot into 50 mL conical tubes. Store at 2° C.-8° C. until use.

| Denature Solution | 5 mL | 2 N NaOH |
|---|---|---|
| | 4 mL | 0.5 M EDTA |
| | 91 mL | RNase/DNase Free H$_2$O |

Filter with 0.2µ cellulose acetate filtration unit. Store at room temp.

| Anti-biotin/HRP 1 mg/mL Conjugate Stock | Redissolve a 0.5 mg bottle of conjugate in 0.5 mL H$_2$O and let sit 15 minutes at room temp. |
|---|---|

Store at 2° C.-8° C. until use. Conjugate is purchased from Jackson ImmunoResearch Laboratories, Inc.

| Wash A | 5 mL | 20X SSC |
|---|---|---|
| | 10 mL | 10% SDS |
| | 985 mL | RNase/DNase Free H$_2$O |
| | pH = | 7.0 ± 0.2 |

Filter with 0.2µ cellulose acetate filtration unit. Store at room temp.

| Wash B | 5 mL | 20X SSC |
|---|---|---|
| | 995 mL | RNase/DNase Free H$_2$O |
| | pH = | 7.0 ± 0.2 |

Filter with 0.2µ cellulose acetate filtration unit. Store at room temp.

Assay Set-up:

Prewarm 1×Hyb buffer at 50° C. for approximately 20 minutes or until fully dissolved before use.

Remove an aliquot of TMB substrate and allow it to warm on the bench to room temperature for at least 15 minutes. To analyze one plate requires 14.4 mL total but do not dispense more than 16 mL per plate to be analyzed.

Prepare sufficient conjugate (15 mL/plate) for the number of plates to be analyzed by diluting the anti-biotin/HRP conjugate stock 1/1000 in 1×Hyb buffer. Leave at room temperature until needed. Diluted conjugate can be used for up to one hour.

Remove a CF plate from the heat-sealed shipping pouch but do not remove the adhesive plate seal before the start of the assay.

Assay Method:

Remove the adhesive plate seal and add 180 uL of 1× hybridization buffer to each well containing a test surface. Replace the plate seal and preheat at 51° C. for 30 minutes in SOLO HT heat block (or equivalent). Initiate Step 2 after 20 minutes of the 30 minutes incubation time.

Caution: Maintaining plate temperature is critical to proper hybridization results. Ambient temperature can impact the temperature of the assay and should be carefully monitored.

Add PCR amplicon sample to a tube or plate and sufficient water to bring the volume to 10 µL total. Add 10 µL of denature solution to the amplicon, mixing up and down with pipetman one time. Incubate at room temperature for 10 minutes.

Remove the plate seal and save. Remove 50 µL of warmed hybridization buffer from each well in the CF plate and add to the denatured PCR product. Mix and take the full volume of denatured PCR product (approximately 70 µL) to the hybridization buffer in the appropriate CF well. Mix thoroughly by repeatedly aspirating and dispensing with the pipetman. Cover the plate with the plate seal. Incubate 10 minutes at 51° C.

Remove the plate from the heat block and remove the plate seal. Wash plate vigorously with stream of Wash A (4 times) followed by a wash with a vigorous stream of Wash B (4 times) at room temperature.

Note: A plate is washed by directing a stream of the appropriate wash solution into the corner of the well until the well is full. After each wash, solution is dumped out. After final wash well is shaken out and the plate is tapped on the bench upside down to remove excess volume or use a plate washer set to a validated program.

5) Add 125 μL of 1 ug/mL anti-biotin antibody/HRP conjugate diluted in hybridization buffer to each well. Incubate uncovered at room temperature 10 minutes.

Wash with vigorous stream of Wash B (6 times).

Add 150 μL TMB substrate to each well. Incubate at room temperature for 5 minutes.

Wash with water (5 times) by filling each well and then dry by adding methanol to fill each well (3 times) and finally blot out excess methanol. Allow the remaining methanol to evaporate before analyzing with the Image Analysis System.

Example 2

This study was designed to determine the performance tolerance of the image analysis station to tilt of a sample to be imaged in the x- and y-directions. A test surface with reacted and unreacted zones was placed on a goniometer that was placed in the optical field at the same depth of field, level of focus, and resolution that would be used in analyzing a test surface in a well of the 96 well plate. The goniometer allows very fine adjustments to the angle of tilt applied to the test surface. The test surface was evaluated with tilt applied to the x- and then the y-direction. Readings for a single reacted spot were taken at various angles of positive and negative tilt, as noted in the following table.

| Tilt Angle | Contrast (Positive-Negative) | Total I |
|---|---|---|
| −10 | 525 | 811 |
| −5 | 843 | 1316 |
| −4 | 914 | 1477 |
| −3 | 920 | 1484 |
| −2 | 992 | 1560 |
| −1 | 990 | 1548 |
| 0 | 1014 | 1496 |
| 1 | 1027 | 1446 |
| 2 | 1028 | 1427 |
| 3 | 1007 | 1361 |
| 4 | 1021 | 1383 |
| 5 | 1001 | 1369 |
| 6 | 1008 | 1363 |
| 7 | 943 | 1247 |
| 8 | 887 | 1156 |
| 10 | 795 | 1058 |

Data is the same in the x - and y - directions.

From −2° to 6° there is less than a 5% loss in contrast. This allows a ±40 process variation at a standard deviation of 3σ, which is excellent tolerance in image station. A slight positional offset of the surface relative to the true 0° position accounts for the fact that the range is not centered at zero.

Example 3

To establish what if any impact ambient light may have on the measured signal intensity of reacted spots using the image analysis station, a plate containing multiple reacted surfaces was placed in the plate holder of the stage and aligned under the camera for imaging. Signal intensity of the various spots on the reacted test surface were measured in the presence and absence of ambient room light. Three reacted surfaces were measured at a polarizer setting of 45° (midpoint) of dial range and a lamp position that is the dial mark just left of the top position and represents a moderate input intensity. Measurements were made at a number of sample positions on different test surfaces. The correlation of individual spot intensities for all spot positions in well C8 with and without room light is 93.7%. The correlation of individual spot intensities for all spot positions in well E8 with and without room light is 94.6%. Thus ambient light appears to have a minimal impact on the analysis of the optical thin film arrays.

Example 4

This study was designed to determine the proper light intensity setting and polarizer position for the image analysis station. A number of individual test surfaces with reacted and unreacted zones in a 96 well plate were selected and then analyzed with various combinations light setting and polarizer position. There is 90° of rotation in the polarizer housing and so the position that causes saturation of signal (no polarization) was labeled as position #1 and is considered a 0° position. The opposing position at 90° from position #1 was labeled as position #2 (and is the 90° position) and the midpoint or 45° of polarizer was labeled as position #3. The light power source has light settings numbered from 1 to 9 with 5 being the mid-point setting.

An acceptable light/polarizer combination will not saturate the background (i.e. produce grayscale values of 4095 with a 12 bit CCD), will show maximal contrast between a negative and a positive spot, will not use fully crossed polarizer setting due to potential loss in signal, will not use the lowest light setting because we could lose signal strength and contrast, will not use the highest light setting due to reducing the lifetime of the lamp, and will use some polarization to balance lighting and defects across the test surface and correct for specular reflection.

The combination of settings tested is given in the following table:

| Condition | Lamp Setting | Polarizer Setting |
|---|---|---|
| 1 | 1 | 0 |
| 2 | 1 | 45 |
| 3 | 1 | 22.5 |
| 4 | 1 | 67.5 |
| 5 | 3 | 0 |
| 6 | 3 | 22.5 |
| 7 | 3 | 45 |
| 8 | 4 | 0 |
| 9 | 4 | 45 |
| 10 | 5 | 0 |
| 11 | 5 | 45 |
| 12 | 6 | 90 |

Overall best lighting conditions are obtained at conditions 4, 8, and 9. All of these conditions give good separation of positive and negative. Conditions 5 and 6 are also possible settings. To more carefully consider the polarizer impact on the data, the data was plotted as gray scale difference versus light setting at the various polarizer settings. Conditions 4 (67.50 Polarizer, Light Setting 1) and 8 (0° Polarizer, Light Setting 4) give the best signal difference but that the signal intensity obtained at a 45° Polarizer setting is fairly independent of the light setting. This is a very favorable condition as minor variations in light intensity can occur over time and with the 45° Polarizer setting should not impact the quality of signal. The light setting impacts signal significantly when no polarizer is used and at full polarizer setting (90°) lower light settings (that would preserve the lamp lifetime and quality) the illumination is insufficient to generate signal.

Although the complete absence of a polarizer, i.e. a 0° setting of the polarizer, is probably acceptable, we selected a 45° setting to use to our advantage the lack of dependence on the light setting at that polarizer setting. Also in the absence of any polarization of the light the system saturates at moderate lamp settings and saturation is not the best condition. A moderate lamp setting appears to give the best over all signal contrast and is the preferred lamp setting. The tolerance to light and polarizer setting is fairly high.

Example 5

A run-to-run reproducibility study was also performed to determine the error involved in setting up the optics recognition and reading a plate. A 96 well plate containing 24 test surfaces was used for this evaluation. Each test surface had a 64-element array as shown in Example 1. The number of spots developed on each test surface was dependent on the genotype of the input sample used in the analysis. The plate designation was 021202.

It is of interest to know the inherent variability involved in the setup of each run. To determine this, one plate was run 5 different times on the same instrument. This involved a fresh setup each time to ensure each run's independence. The correlation between each separate run was calculated using the correlation data analysis package on Excel. The correlation ρ is calculated using the covariance and the respective standard deviations in the following manner.

$$\rho_{X,Y} = \frac{\mathrm{Cov}(X,Y)}{\sigma_X * \sigma_Y}$$

This procedure was performed on plate 021202, a very clean plate with aligned and separate spots. This plate has test surface in 3 rows: A, D, and H. This plate was run incorporating a test surface-straightening function and a spot-finding function. The test surfaces on plate 021202 do not all carry the same homozygous/heterozygous mutations. To account for this difference, data points for the mutation/missing wild type spots were disregarded in homozygous test surfaces in the averaging for that particular spot. Mutation spots were eliminated in heterozygous spots. For the spots 5T, 7T and 9T, since most of the chips showed a 7T spot, the 5T and 9T spots were eliminated where they appeared and those that did not show 7T were also disregarded. Spots 4 and 6 do not show up whereas spot 5 does. In other words, the response of the majority was maintained. With this elimination of inconsistent spots, the correlation data was calculated and tabulated in the following table:

|  | Row 1 | Row 2 | Row 3 | Row 4 | Row 5 |
|---|---|---|---|---|---|
| Row 1 | 1 | | | | |
| Row 2 | 99.962% | 1 | | | |
| Row 3 | 99.987% | 99.987% | 1 | | |
| Row 4 | 99.959% | 99.907% | 99.929% | 1 | |
| Row 5 | 99.994% | 99.957% | 99.982% | 99.957% | 1 |

The correlation between runs for plate 021202 is excellent. The smallest correlation being 99.907% between run 4 and run 2. All of these small differences fall within the standard deviation obtained.

The run-to-run consistency is very good. The correlation calculated shows that the largest discrepancy on plate 021202 is between run 3 and 2 and is on the order of 0.8%. This and any other differences are more than accounted for in the standard deviation involved in averaging across spots. These results convey that any discrepancies in data between plates are most likely not due to inconsistencies in setting the optical lamp or the manual alignment performed by the operator. This is true as long as several operating guidelines from the user's manual are followed. The alignment must be made to fit the spots into the alignment grid squares as well as possible.

Example 6

The goal of this experiment was to validate the use of a new spot finding algorithm for image analysis. The spot finding algorithm was designed to allow for greater versatility of spot positioning by locating spots outside the default placement of a grid. This functionality was tested with the corner test surfaces (corners of the 96 well plate) systematically misaligned at the beginning of a run. The plate analyzed contains optical thin film test surfaces spotted with the CF array shown in Example 1. Interpretations of the signals were done with a software package developed for classification of the sample genotypes. For this experiment, reported classifications are compared to the known genotype of the input sample. A comparison of consistency in performance before and after the incorporation of this new software algorithm will be examined to establish any loss in functionality compared to the original spot finding routine. Both the interpretation of spot signal and intensity values will be considered when making these comparisons.

This study was conducted with the image analysis system described above and a 96 well plate designated EW042502. The plate was analyzed separately eight times while varying the initial alignment position. The light intensity was set once and remained the same throughout. The initial alignment grid was adjusted systematically on the 4 corner test surfaces while maintaining the edges of the test surface in the image.

Run 1—normal alignment: grid is positioned so as to squarely encompass the array of dots.

Run 2—grid was placed to the left of the spots at each of the four corner wells.

Run 3—grid was placed to the right of the spots

Run 4—grid was placed above the spots

Run 5—grid was placed below the spots

Run 6—grid was placed diagonally up and to the left

Run 7—grid was placed diagonally outwards from the spots on each of the 4 corners. Well A1 was up and left of the spots, well A12 was up and right of the spots, well H1 down and left of the spots and well H12 down and right of the spots.

Run 8—grid was placed diagonally inwards from the spots on each of the 4 corners. Well A1: down/right, well A12: down/left, well H1: up/right, well H12: up/left.

After each misalignment, the plate was run and classified for genotype. The resulting data was compared to determine whether the spot finding algorithm had in fact adjusted for the misalignment compensating for the error. Both data on genotype calls and intensity values are used in the comparison.

Several discrepancies arose in the genotype classification. There was no trend corresponding to type of misalignment. A table of the number of erroneous gentoype classifications for each run can be found in the following table:

| Run Number | # of Errors |
|---|---|
| 1 | 1 |
| 2 | 3 |
| 3 | 2 |
| 4 | 8 |
| 5 | 0 |
| 6 | 1 |
| 7 | 3 |
| 8 | 6 |

These false calls all were given an error code of 24 except one, well A4. Code 24 indicates a well containing a test surface with undefined edges. This can be caused by the edge being outside the imaged area, reflection of the plastic well sides, shadowing or broken chips in which the edges and corners of the chip are not crisp lines. The exception, well A4, was interpreted identically in all the runs except for run 3. Extra glue from manufacture provides a sporadic problem that is addressed in conjunction with the process for test surface positioning within the carrier.

For the qauntitative data analysis, wild type coefficient of variation ("CV") values were calculated for each of the runs as well as across all runs together. There does not appear to be a correlation of type of misalignment to the type of error generated. For example, run 1 (normal) alignment made 1 error where as run 4 (grid below spots) had no failures. All the errors (except for well A4, run 3) are of a 24 type which is reserved for "bad chips". These are test surface without crisply defined edges and corners. Having the 4 corner wells so substantially skewed created shadowing/reflection effects affecting edges in these cases. This is an issue outside the scope of the spot finding algorithm.

Figure 14:
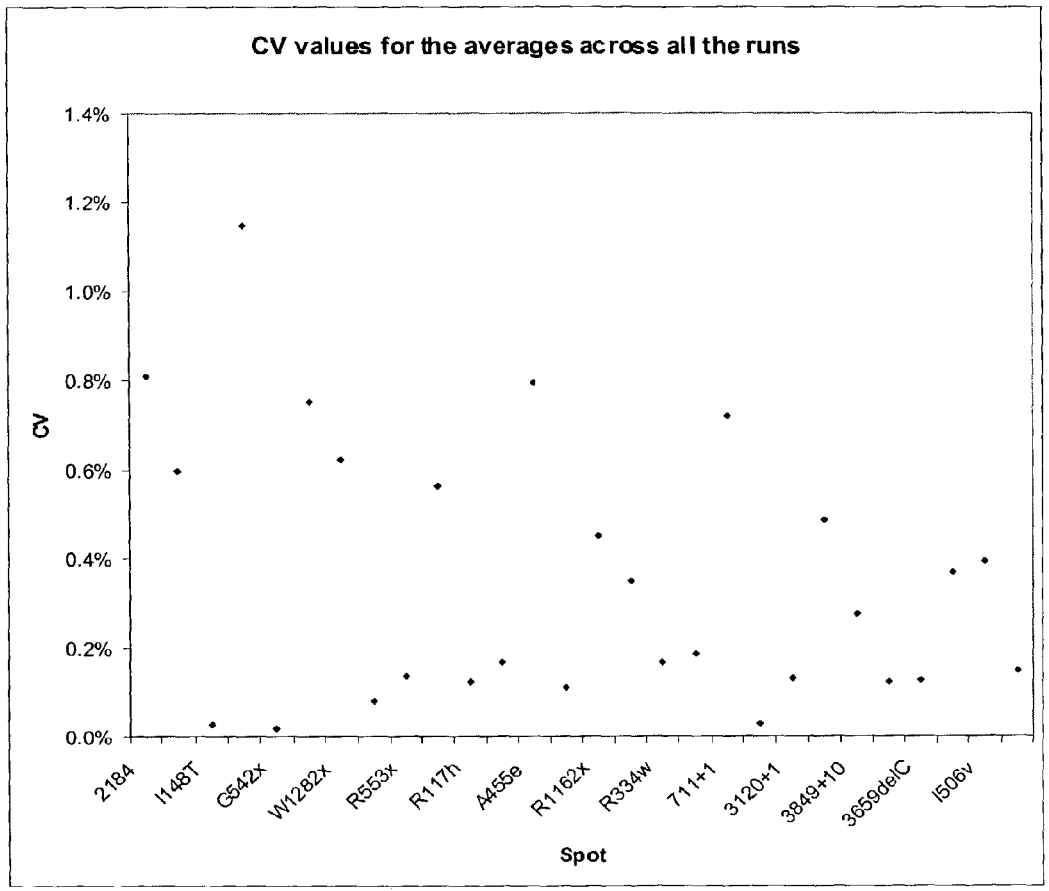
FIG. 14 illustrates exemplary CV values for the average of all spots for a set of runs.

The CV values for the different results follow a very similar trend. The CV between the average of all the runs is shown in FIG. 14, the maximum deviation being 1.2%. This result indicates an equivalency in the interpretations in spite of the wells being located at different locations of the image.

Figure 15:
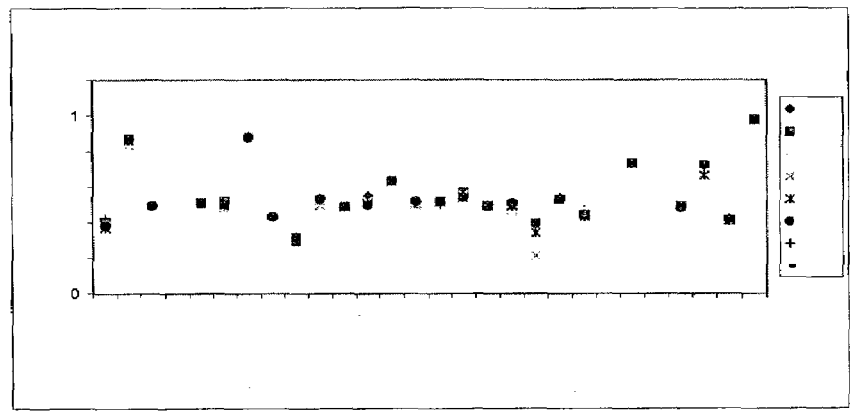
FIG. 15 illustrates the intensity ratio for a set of runs.

FIG. 15 illustrates the intensity ratio (background to signal) for each of the separate runs. Once again, this data follows a similar trend. The largest deviation is in spot 711+1 in which the ratio for run 3 was almost 0.2 units lower than that for run 5. It is expected that this interval would tighten with the consideration of more data.

Figure 16:
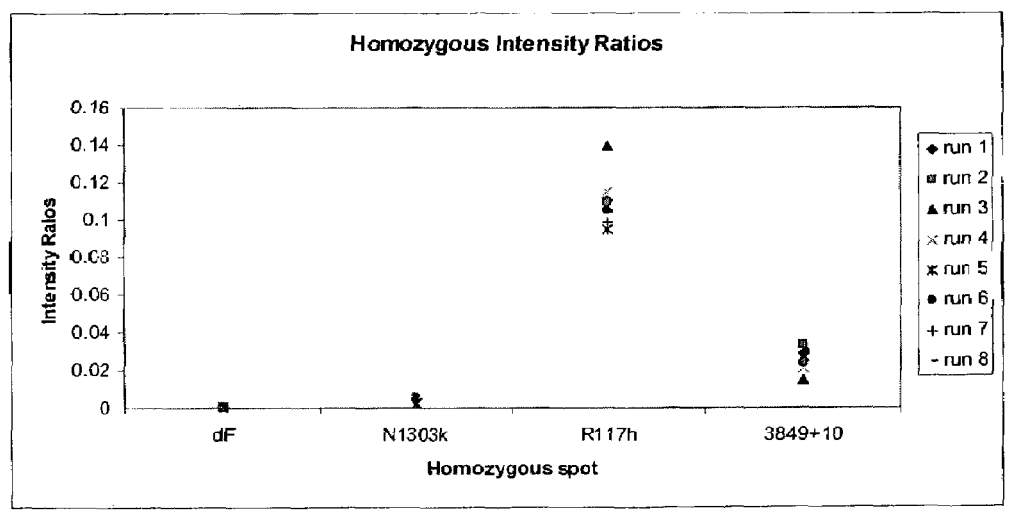
FIG. 16 illustrates the information illustrated in FIG. 15 for homozygous spots.

FIG. 16 shows the same graph for the homozygous spots. Here the largest difference is between run 3 and run 8 and is on the order of 0.04 units.

The differences shown above are within those expected in a reproducibility study. This illustrates the spot finding algorithm is able to locate spots when these are not in the expected domain.

The flexibility to find spots in variable locations and for different magnifications demonstrated above for less than ideal situations shows that the incorporation of this algorithm is an improvement in the overall process.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analyte;

wherein said signal is determined simultaneously from each of said plurality of discrete test locations on one of said discrete arrayed optical thin film test surfaces by capturing an image of a discrete arrayed optical thin film test surface, and performing image analysis on said image to obtain a signal from each of said plurality of discrete test locations; and wherein said image analysis comprises:

identifying an initial array location in the image of the arrayed optical thin film test surface, identifying whether skew or flatness is present and correcting for skew and flatness if present;

thresholding the image;

identifying individual test locations in the thresholded image and refining the array location by comparing an offset of the location of each test location to a predicted test location obtained from the initial array location; and obtaining a signal from each test location in the refined array.

2. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of the arrayed optical thin film test surface on the test surface carrier is identified by a method comprising:

a) acquiring an electronic image of said test surface;

b) squaring said image to orient columns and rows of pixels in a substantially vertical and horizontal configuration, respectively, said squaring comprising:

detecting edges of said image, said detecting comprising forming a first vector of pixel sums for a set of columns of pixels in said image; forming a second vector of pixel sums for a set of rows of pixels in said image; generating a squared first derivative of said first and second vectors; and detecting peaks in said squared first derivatives; and rotating said image;

c) locating a grid of said columns and rows of said image; and d) binarizing said image using a threshold value of signal strength to identify location of spots on said grid.

3. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of an arrayed optical thin film test surface on a test surface carrier is identified by a method comprising:

a) acquiring an electronic image of said test surface;

b) squaring said image to orient columns and rows of pixels in a substantially vertical and horizontal configuration, respectively;

c) locating a grid of said columns and rows of said image, wherein said locating comprises detecting a grid of signal peaks corresponding to rows and columns of said grid, said detecting the grid comprising the steps of generating second derivatives of inverted pixel sums, and locating minima of said second derivatives; and d) binarizing said image using a threshold value of signal strength to identify location of spots on said grid.

4. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of the arrayed optical thin film test surface on the test surface carrier is identified by a method comprising:

a) generating gradients for an image in two substantially orthogonal directions;

b) generating a squared gradient magnitude corresponding to said generated gradients;

c) binarizing said gradient magnitude using a threshold value of said squared gradient magnitude;

d) generating a transform image based on said gradients;

e) binarizing said transform image using a threshold value of a maximum vote count for the transform of step d) to produce a thresholded transform image;

f) detecting contiguous groups of pixels in said thresholded transform image;

g) building a grid to correspond to a layout of said array;

h) measuring signal strength at spot locations of said grid; and i) generating a table of spot positions and signals, said spot positions being indicative of a spot center.

5. The method according to claim 4, further comprising:
detecting edges of said test surface prior to step a); and
cropping said image to said detected edges.

6. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of the arrayed optical thin film test surface on the test surface carrier is identified by a method comprising:

a) acquiring an electronic image of said test surface;

b) squaring said image to orient columns and rows of pixels in a substantially vertical and horizontal configuration, respectively;

c) locating a grid of said columns and rows of said image, wherein said location is identified by using a program product comprising machine readable program code for causing a machine to perform following method steps:

i) squaring said test surface to orient columns and rows of pixels in a substantially vertical and horizontal configuration, respectively, said squaring comprising using program code for causing a machine to perform the following step:

detecting edges of said image wherein said detecting edges comprises using a program code for causing a machine to perform the steps of: forming a first vector of pixel sums for a set of columns of pixels in said image; forming a second vector of pixel sums for a set of rows of pixels in said image; generating a squared first derivative of said first and second vectors; and detecting peaks in said squared first derivatives; and rotating said image;

ii) locating a grid of said columns and rows of said image; and d) binarizing said image using a threshold value of signal strength to identify location of spots on said grid.

7. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of the arrayed optical thin film test surface on the test surface carrier is identified by a method comprising:

a) acquiring an electronic image of said test surface;

b) squaring said image to orient columns and rows of pixels in a substantially vertical and horizontal configuration, respectively;

c) locating a grid of said columns and rows of said image, wherein said location is identified by using a program product comprising machine readable program code for causing a machine to perform following method steps:

i) squaring said test surface to orient columns and rows of pixels in a substantially vertical and horizontal configuration, respectively;

ii) locating a grid of said columns and rows of said image, said locating a grid comprising using program code for causing a machine to perform the step of detecting of a grid of signal peaks corresponding to rows and columns of said grid, said detecting of a grid of signal peaks comprising using program code for causing the machine to perform the steps of generating second derivatives of inverted pixel sums, and locating minima of said second derivatives; and d) binarizing said image using a threshold value of signal strength to identify location of spots on said grid.

8. A method for determining the presence or amount of a plurality of analytes in one or more samples using a test surface carrier comprising a plurality of discrete arrayed optical thin film test surfaces, each arrayed optical thin film test surface comprising a plurality of discrete test locations comprising a capture reagent to immobilize for detection of one of said analytes, said method comprising:

contacting each of said discrete arrayed optical thin film test surfaces with a sample to be tested for said plurality of analytes, whereby said analytes, if present, are immobilized at a corresponding test location;

removing unbound sample components from each of said discrete arrayed optical thin film test surfaces; and determining a signal from each of said plurality of discrete test locations on each of said discrete arrayed optical thin film test surfaces, wherein each of said signals is related to a change in mass or optical thickness of the corresponding optical thin film, each of said signals comprising light reflected from the surface that has undergone a change in the polarization state, phase or interference color, and relating each of the signals to the presence or amount of one of said plurality of analytes;

wherein the location of the arrayed optical thin film test surface on the test surface carrier is identified by using a program product comprising a machine readable program code for causing a machine to perform the following method steps:

a) generating gradients for an image in two substantially orthogonal directions;

b) generating a squared gradient magnitude corresponding to said generated gradients;

c) binarizing said gradient magnitude using a threshold value of said squared gradient magnitude;

d) generating a transform image based on said gradients;

e) binarizing said transform image using a threshold value of a maximum vote count for the transform of step d) to produce a thresholded transform image;

f) detecting contiguous groups of pixels in said thresholded transform image;

g) building a grid to correspond to a layout of said array;

h) measuring signal strength at spot locations of said grid; and i) generating a table of spot positions and signals, said spot positions being indicative of a spot center.

9. The method according to claim 8, wherein said program code causes a machine to further perform the following method steps:

detecting edges of said test surface prior to step a); and cropping said image to said detected edges.

* * * * *

UNITED STATES PATENT AND TRADEMARK OFFICE
CERTIFICATE OF CORRECTION

| | | |
|---|---|---|
| PATENT NO. | : 7,522,762 B2 | Page 1 of 1 |
| APPLICATION NO. | : 10/417883 | |
| DATED | : April 21, 2009 | |
| INVENTOR(S) | : Rea et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1114 days.

Signed and Sealed this
Seventh Day of June, 2011

David J. Kappos
*Director of the United States Patent and Trademark Office*